(12) United States Patent
Eberhardt et al.

(10) Patent No.: US 10,273,213 B2
(45) Date of Patent: Apr. 30, 2019

(54) METHOD FOR THE PRODUCTION OF PRAZIQUANTEL AND PRECURSORS THEREOF

(71) Applicant: Merck Patent GmbH, Darmstadt (DE)

(72) Inventors: Luc Eberhardt, Wiesbaden (DE);
Andreas Waechtler, Darmstadt (DE);
David Maillard, Darmstadt (DE);
Stefan Lehmann, Otzberg (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/756,267

(22) PCT Filed: Aug. 10, 2016

(86) PCT No.: PCT/EP2016/001376
§ 371 (c)(1),
(2) Date: Feb. 28, 2018

(87) PCT Pub. No.: WO2017/036577
PCT Pub. Date: Mar. 9, 2017

(65) Prior Publication Data
US 2018/0251428 A1    Sep. 6, 2018

(30) Foreign Application Priority Data

Sep. 1, 2015 (EP) .................................... 15183283

(51) Int. Cl.
| C07D 217/14 | (2006.01) |
| C07B 53/00 | (2006.01) |
| B01J 31/12 | (2006.01) |
| B01J 31/24 | (2006.01) |
| C07D 401/04 | (2006.01) |

(52) U.S. Cl.
CPC .......... *C07D 217/14* (2013.01); *B01J 31/122* (2013.01); *B01J 31/249* (2013.01); *B01J 31/2409* (2013.01); *B01J 31/2452* (2013.01); *C07B 53/00* (2013.01); *C07D 401/04* (2013.01); *B01J 2531/0266* (2013.01); *B01J 2531/827* (2013.01)

(58) Field of Classification Search
None
See application file for complete search history.

(56) References Cited

U.S. PATENT DOCUMENTS 3,985,881 A    10/1976 Mehrhof
4,362,875 A    12/1982 Seubert

FOREIGN PATENT DOCUMENTS

DE    2504250 A1    8/1976
WO    2013/127354    *    9/2013

OTHER PUBLICATIONS

Cedillo-Cruz, Tetrahedron: Asymmetry, 25 (2014), 133-140. (Year: 2014).*
International Search Report PCT/EP2016/001376 dated Sep. 26, 2016.
Roszkowski P et al: "Enantioselective synthesis of (R)-(−)-praziquantel (PZQ)", Tetrahedron Asymmetry, Pergamon Press Ltd, Oxford, GB, vol. 17, No. 9, May 15, 2006 (May 15, 2006), pp. 1415-1419, XP024962076, ISSN: 0957-4166, [retrieved on May 15, 2006].
Sadhu Partha Sarathi et al: "Synthesis of new praziquantel analogues: Potential candidates for the treatment of schistosomiasis", Bioorganic & Medicinal Chemistry Letters, Pergamon, Amsterdam, NL, vol. 22, No. 2, Dec. 13, 2011 (Dec. 13, 2011), pp. 1103-1106, XP029121656, ISSN: 0960-894X.
Althea S.-K. Tsang et al: "Enhancing the usefulness of cross dehydrogenative coupling reactions with a removable protecting group", Organic & Biomolecular Chemistry, vol. 11, No. 30, Jan. 1, 2013 (Jan. 1, 2013), GB, pp. 4921, XP055300970, ISSN: 1477-0520.
Alexander Dömling et al: "Praziquantel and Schistosomiasis", Chemmedchem, vol. 5, No. 9, Aug. 2, 2010 (Aug. 2, 2010), DE, pp. 1420-1434, XP055301198, ISSN: 1860-7179.

* cited by examiner

*Primary Examiner* — D Margaret M Seaman
(74) *Attorney, Agent, or Firm* — Millen White Zelano and Branigan, PC; Csaba Henter

(57) ABSTRACT

The present invention provides methods of preparing Praziquantel, in particular (R)-Praziquantel and analogues thereof in a stereoselective manner. One method involves asymmetric hydrogenation of the following intermediate compound and subsequent cyclization.

20 Claims, No Drawings

METHOD FOR THE PRODUCTION OF PRAZIQUANTEL AND PRECURSORS THEREOF

FIELD OF THE INVENTION

The present invention relates to a method for preparing Praziquantel and precursors and analogues thereof, and in particular enantiomerically pure or enantiomerically enriched Praziquantel and precursors and/or analogues thereof.

BACKGROUND OF THE INVENTION

Schistosomiasis is an acute and chronic disease caused by parasitic worms. According to the WHO, it affects almost 240 million people worldwide, and more than 700 million people live in endemic areas. Several million people all over the world suffer from severe morbidity as a consequence of schistosomiasis. Praziquantel is currently the only recommended drug for infection and disease caused by the species of schistosome infecting humans.

Praziquantel (PZQ) was registered, approved and commercialized in the beginning of the 1980's as a racemic mixture. However, it has turned out that only the (R)-enantiomer is active (eutomer) (P. Andrews, H. Thomas, R. Pohlke, J. Seubert Medical Research Reviews 3, 147(1983)).

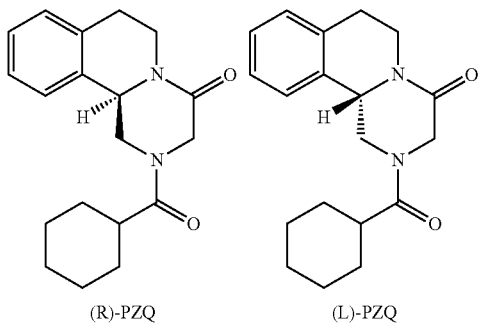

(R)-PZQ        (L)-PZQ

Racemic Praziquantel has a repugnantly bitter taste. This leads to acceptance issues—in particular in the treatment of young children. In addition to the difference in activity, the (R)-Praziquantel eutomer is also considered to have a less bitter taste than the (S)-Praziquantel distomer (T. Meyer et al. (2009) PLoS Negl Trop Dis 3(1): e357). Thus, there is a desire for an economical manufacturing process that is suitable to prepare enantiomerically enriched or preferably even pure (R)-Praziquantel.

During the past decades, numerous attempts were made to develop a manufacturing process for (R)-Praziquantel or its analogues. These attempts can be divided into two groups, firstly enantioselective synthesis routes, and secondly methods producing a racemic mixture in combination with chiral resolution. Given that the latter approach necessarily involves additional process steps, a process leading directly to (R)-Praziquantel might principally be more attractive. However, identifying a suitable enantioselective route of synthesis that is economically attractive has proven very difficult. The pursuit of such a synthesis as well as other methods of economically manufacturing (R)-Praziquantel is still ongoing.

DESCRIPTION OF THE INVENTION

It is therefore an object of the present invention to provide an efficient method for the preparation of Praziquantel and analogues thereof that is suitable to provide enantiomerically enriched or enantiomerically pure (R)-Praziquantel or analogues thereof, and in particular a suitable stereoselective route of synthesis that allows the preparation of enantiomerically enriched or even enantiomerically pure (R)-Praziquantel or analogues thereof without necessarily requiring chiral separation. Nonetheless, it is a further object of the present invention to provide an advantageous method for preparing desired enantiomers both in terms of final product and intermediate product, including mixtures of enantiomers with a more favourable percentage of desired enantiomer as compared to the starting material.

This object has surprisingly been solved by a novel route of synthesis, which allows a stereoselective synthesis of (R)-Praziquantel and analogues thereof. The novel route of synthesis has been rendered possible as a result of the identification and preparation of a novel key intermediate compound. Apart from the stereoselective synthesis, the key intermediate compound also opens up possibilities of non-stereoselective synthetic routes toward racemic or enantiomerically enriched or pure Praziquantel of analogues thereof that are considered advantageous. Of course, the present invention is not limited to Praziquantel itself, but equally applicable to analogues thereof. The present invention also provides an attractive recycling method for any reaction side-product or less than ideal enantiomer or enantiomer mixture, as will be set out below.

In particular, the present invention provides, under a first aspect, a method of preparing
(i) an optically active compound according to the following Formula (X1)

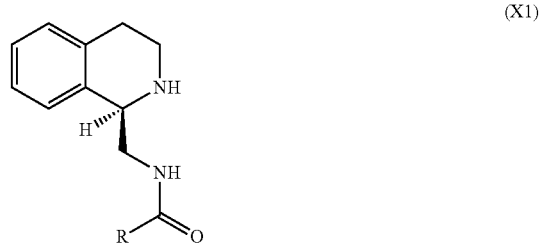

(X1)

or
(ii) an optically active compound according to the following Formula (X2)

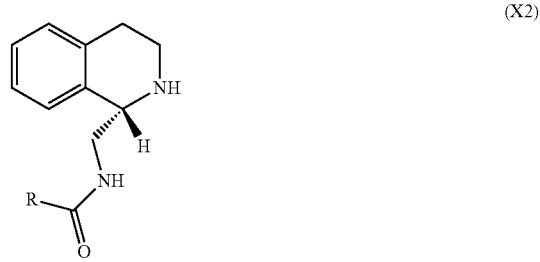

(X2)

or (iii) a mixture of the two,
wherein in Formula (X1) and Formula (X2), R is selected from $C_1$-$C_8$ alkyl, $C_{3-8}$ cycloalkyl, and optionally substituted aryl,
comprising: subjecting a compound according to the following Formula (Y)

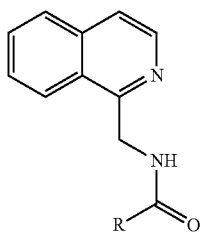

(Y)

with R as above, to a hydrogenation step.

Needless to mention, the moiety R is the same in the compound according to Formula (Y) and the compounds according to Formulae (X1) and (X2).

$C_1$-$C_8$ Alkyl, $C_{3-8}$ cycloalkyl, and aryl have the usual meaning in the art: $C_1$-$C_8$ Alkyl encompasses straight (unbranched) or branched alkyl groups having 1, 2, 3, 4, 5, 6, 7 or 8 C-atoms, for instance methyl, ethyl, n-propyl, iso-propyl, butyl, tert-butyl, pentyl, hexyl, heptyl and octyl, with methyl and ethyl being the most preferred. $C_3$-$C_8$ Cycloalkyl encompasses saturated cyclic hydrocarbon ring systems having 3, 4, 5, 6, 7 or 8 ring C-atoms and encompasses cyclopropyl, cyclobutyl, cyclopentyl, cyclohexyl, cycloheptyl, and cyclooctyl, with cyclohexyl being most preferred. Aryl encompasses aromatic carbocyclic ring systems, phenyl being an exemplary embodiment, wherein the aryl may be unsubstituted or substituted, such as by one, two or more substituents selected from amino, acylamino wherein the acyl group may contain up to four carbon atoms, halogen, hydroxy, methoxy, or nitro.

In preferred embodiments of the present invention, R is methyl or cyclohexyl, most preferably cyclohexyl. Cyclohexyl is obviously preferred as it allows subsequent direct synthesis of Praziquantel. Equally for the synthesis of (R)-Praziquantel, it is preferred that the method according to claim 1 produces the compound according to Formula (X1), which has the (R)-configuration, or a mixture of the compounds according to Formulae (X1) or (X2), wherein the compound according to Formula (X1) is present in an excess (as compared to the compound according to Formula (X2)). Hence, the method according to claim 1 preferably produces the compound of Formula (X1) in either enantiomerically enriched or enantiomerically pure form.

In most preferred embodiments of the present invention, in the method of preparing an optically active compound according to Formula (X1) or Formula (X2) or a mixture of the two, the hydrogenation step is an asymmetric hydrogenation step in the presence of a catalyst and, if a mixture of optically active compounds according to Formula (X1) or Formula (X2) is obtained, the mixture comprises either the compound according to Formula (X1) or the compound according to Formula (X2) in excess. In other words, the asymmetric hydrogenation yields enantiomerically enriched or enantiomerically pure compounds according to Formula (X1) or Formula (X2).

Preferably, the compound according to Formula (X1) or Formula (X2) is present in the mixture in an enantiomeric excess of at least 10%, preferably at least 20%, more preferably at least 30%, at least 40%, at least 50%, at least 60%, at least 70%, at least 80%, or evidently most preferably at least 85%, at least 90%, at least 95% or 100%. In the preparation of (R)-Praziquantel, the compound of Formula (X1) is typically the desired intermediate.

Advantageously, the catalyst used in the asymmetric hydrogenation is an iridium based catalyst. However, the use of other catalysts, such as rhodium or ruthenium, may also be feasible.

Preferably, the iridium based catalyst consists of or comprises iridium in combination with a chiral ligand. More preferably, the iridium based catalyst consists of or comprises a mixture of an iridium compound, such as [Ir(COD)Cl]$_2$, and a chiral phosphine ligand. For the purpose of the present invention, a chiral phosphine ligand shall encompass any ligand comprising a phosphine moiety and comprising a centre of chirality. For instance, the iridium based catalyst consists of or comprises a mixture of an iridium compound, such as [Ir(COD)Cl]$_2$, and a ligand chosen from the Josiphos ligand family, the BoPhoz ligand family, the Taniaphoz ligand family, the BINAP patent family, and other ligands, as described and illustrated below. Preferably, the iridium based catalyst consists of or comprises a mixture of an iridium compound, such as [Ir(COD)Cl]$_2$ and one of the following ligands:

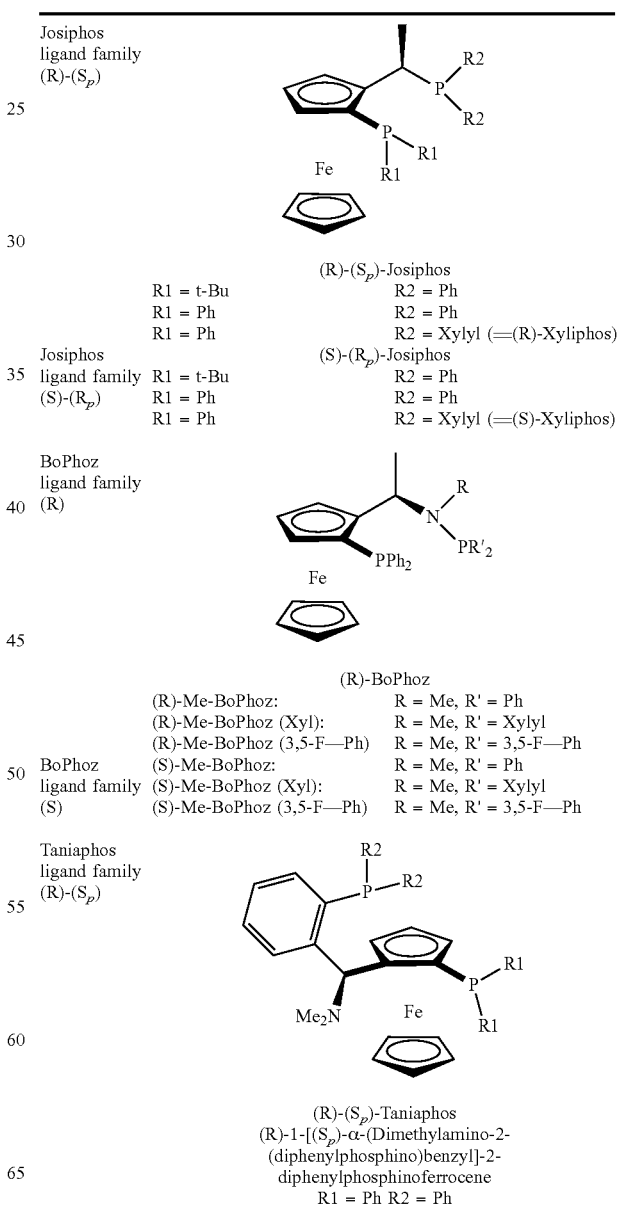

| | |
|---|---|
| Taniaphos ligand family (S)-(R$_p$) | (S)-(R$_p$)-Taniaphos<br>(S)-1-[(R$_p$)-α-(Dimethylamino-2-(diphenylphosphino)benzyl]-2-diphenylphosphinoferrocene<br>R1 = Ph R2 = Ph |
| BINAP ligand family (R) | 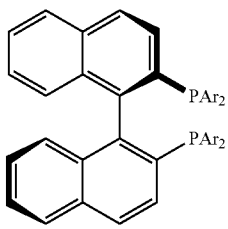<br>(R)-Xylyl-BINAP<br>Ar = 3,5-Me$_2$—Ph |
| BINAP ligand family (S) | (S)-Xylyl-BINAP<br>Ar = 3,5-Me$_2$—Ph |
| | 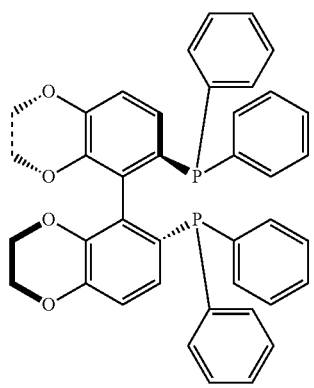<br>(R)-6,6'-Bis(diphenylphosphino)-2,2',3,3'-tetrahydro-5,5'-bi-1,4-benzodioxine<br>(S)-6,6'-Bis(diphenylphosphino)-2,2',3,3'-tetrahydro-5,5'-bi-1,4-benzodioxine |
| | 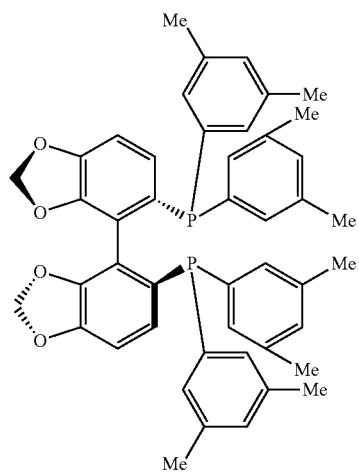<br>(S)-5,5'-Bis(di(3,5-xylyl)phosphino)-4,4'-bi-1,3-benzodioxole<br>(R)-5,5'-Bis(di(3,5-xylyl)phosphino)-4,4'-bi-1,3-benzodioxole |

| |
|---|
| 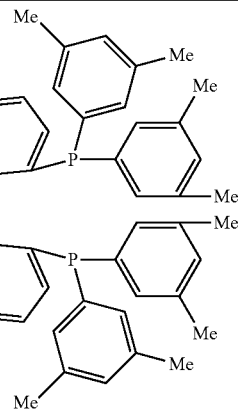<br>(R)-7,7'-Bis[di(3,5-dimethylphenylphosphino]-2,2',3,3'-tetrahydro-1,1'-spirobiindane<br>(S)-7,7'-Bis[di(3,5-dimethylphenylphosphino]-2,2',3,3'-tetrahydro-1,1'-spirobiindane |
| 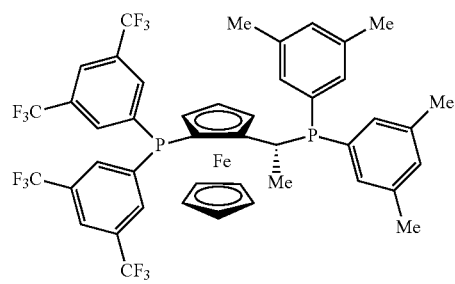<br>(R)-1-{(S)-2-[Bis[3,5-di-trifluoromethylphenyl)phosphino]ferrocenyl}ethyldi-3,5-xylylphosphine<br>(S)-1-{(R)-2-[Bis[3,5-di-trifluoromethylphenyl)phosphine]ferrocenyl}ethyldi-3,5-xylylphosphine<br>(R)-C3-TunePhos<br>(R)-1,13-Bis(diphenylphosphino)-7,8-dihydro-6H-dibenzo[f,h][1,5]dioxonin<br>(S)-C3-TunePhos<br>(S)-1,13-Bis(diphenylphosphino)-7,8-dihydro-6H-dibenzo[f,h][1,5]dioxonin |

Out of the Josiphos patent family, the following ligands are preferred:

| |
|---|
| A |
| 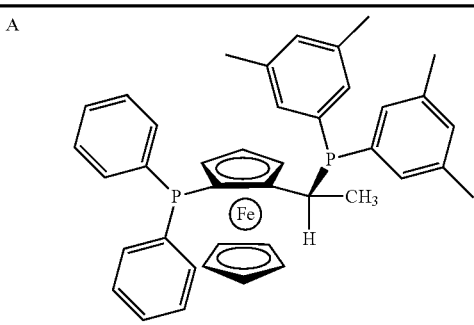<br>(R)-1-[(S)-2-Diphenylphosphino)-ferrocenyl]ethyl-di-3,5-xylylphosphine<br>(R)-1-[(S$_p$)-2-Diphenylphosphino)-ferrocenyl]ethyl-di-3,5-xylylphosphine<br>Abbreviated herein: (R)-Xyliphos |

| | |
|---|---|
| B | 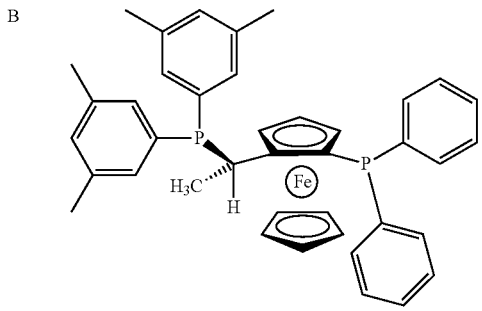<br>(S)-1-[(R)-2-Diphenylphosphino)-ferrocenyl]ethyl-<br>di-3,5-xylylphosphine<br>(S)-1-[(R$_p$)-2-Diphenylphosphino)-ferrocenyl]ethyl-<br>di-3,5-xylylphosphine<br>Abbreviated herein: (S)-Xyliphos |
| C | (R)-1-[(S$_p$)-2-Diphenylphosphino)-ferrocenyl]ethyl-<br>diphenylphosphine |
| D | (S)-1-[(R$_p$)-2-Diphenylphosphino)-ferrocenyl]ethyl-<br>diphenylphosphine |

As is common general knowledge in the art, if a certain enantiomer in a catalyst system, e.g. the (R) enantiomer in the catalyst system, allows to produce a certain enantiomer of the hydrogenated product, e.g. the (S) enantiomer, the respective other enantiomer of the catalyst system, e.g. the (S) enantiomer in this example, will lead to the respective other enantiomer of the hydrogenated product, e.g. the (R) enantiomer in the present example.

In the synthesis of the compound according to Formula (X1) wherein R is cyclohexyl, the following ligands are preferably used:
(S)-Xyliphos, (R)-1-[(S$_p$)-2-Diphenylphosphino)-ferrocenyl]ethyl-diphenylphosphine, (R)-1-[(S$_p$)-α-(Dimethylamino-2-(diphenylphosphino)benzyl]-2-diphenylphosphino-ferrocene and (R)-Xylyl-BINAP. These ligands are further preferably used together with an additive, for instance iodine, for instance in an amount of at least 5 mol %, more preferably at least 50 mol % or at least 100 mol %.

[Ir(COD)Cl]$_2$ stands for cyclooctadiene iridium chloride dimer, which is illustrated by the following structure:

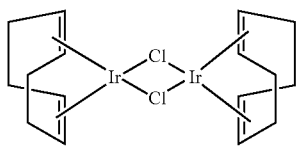

In exemplary embodiments, the asymmetric hydrogenation step in the presence of a catalyst is carried out involving at least one of:
  elevated temperature, which temperature is preferably at least 60° C., for instance at least 80° C., at least 90° C. or at least 100° C.;
  a solvent selected from dioxane, THF, Me-THF, IPA, DCE, DCM, ethyl acetate, toluene, α,α,α-trifluorotoluene, xylene, preferably m-xylene or p-xylene, mesitylene or a mixture of any two or more thereof;
  at least one additive, which is preferably selected from iodine (I$_2$), iodide, phosphoric acid (H$_3$PO$_4$), acetic acid (AcOH), HI, HBF$_4$, preferably in an amount of at least 5 mol %, more preferably at least 50 mol %, more preferably at least 100 mol %;
  a substrate concentration of at least 0.05 mmol/l, for instance at least 10 mmol/l, at least 100 mmol/l;
  a catalyst loading of at least 50/1 substrate/catalyst; for instance at least 100/1, at least 250/1, at least 500/1 and
  normal to elevated pressure, which pressure is preferably at least 1 bar H$_2$, at least 5 bar H$_2$, at least 10 bar H$_2$, at least 20 bar, at least 25 bar H$_2$, at least 50 bar or at least 100 bar H$_2$.

In a preferred embodiment, [Ir(COD)Cl]$_2$ is used in combination with (S)-Xyliphos in the presence of an additive, such as iodine (I$_2$) or HI. In a further preferred embodiment, [Ir(COD)Cl]$_2$ is used in combination with (R)-Xylyl-BINAP in the presence of an additive, such as iodine (I$_2$) or HI. These catalysts/ligands are particularly preferred if R is cyclohexyl, i.e. in the preparation of Praziquantel and its precursors.

Use of transfer hydrogenation reaction conditions may be a feasible alternative for the asymmetric hydrogenation reaction. For instance, a transfer hydrogenation of compound (Y) to give compound (X1) with R=cyclohexyl may use (S,S)-Ts-DPEN RhCp*Cl (which stands for [N-[(1S, 2S)-2-(Amino-κN)-1,2-diphenylethyl]-4-methylbenzenesulfonamidato-κN]chloro[(1,2,3,4,5,6-η)-1-methyl-4-(1-methylethyl)benzene]-rhodium) and HCOOH, triethylamine 5/2 as a reductant in excess. Use of the following reaction conditions: Additive KI (50 mol %), no solvent, 40° C., 0.1 mmol, catalyst loading 100/1 S/C, 16 hours, gave 100% conversion with a fairly modest enantiomeric excess of 17% (R)-enantiomer (X1 vs. X2 compound).

In an alternative embodiment, a compound according to Formula (Y) can be subjected to a hydrogenation step, in particular a non-selective hydrogenation step, to prepare a mixture of the compounds, in particular racemic mixture of compounds according to Formulae (X1) and (X2). This mixture of compounds can then be used to prepare racemic Praziquantel or analogues thereof, or be subjected to chiral resolution to prepare the respective enantiomerically pure or enantiomerically enriched compound of Formula (X1) or (X2).

Such a hydrogenation step, in particular non-stereoselective hydrogenation step, can be carried out using any known suitable conventional hydrogenation reaction processes, such as those processes involving the use of hydrogen in the presence of a suitable catalyst, such as Pt—C or Pd—C.

In a further aspect, the present invention provides a method of preparing an enantiomerically pure or enantiomerically enriched compound according to Formula (Q1) or Formula (Q2)

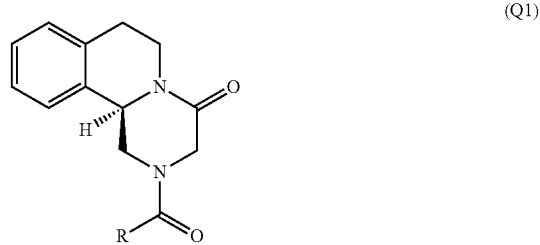

(Q1)

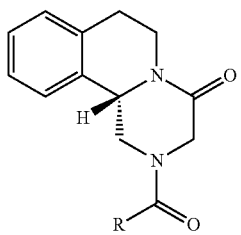

(Q2)

comprising (a) preparing (i) the optically active compound according to the Formula (X1) or (iii) the mixture of compounds according to Formula (X1) and Formula (X2), in which mixture the compound according to Formula (X1) is present in excess, according to the method of the present invention, for the preparation of the compound according to Formula (Q1)

or (b) preparing (i) the optically active compound according to the Formula (X2) or (iii) the mixture of compounds according to Formula (X1) and Formula (X2), in which mixture the compound according to Formula (X2) is present in excess, according to the method of the present invention, for the preparation of the compound according to Formula (Q2).

In the compounds of Formulae (Q1) and (Q2), R is selected from $C_1$-$C_8$ alkyl, $C_3$-$C_8$ cycloalkyl, and optionally substituted aryl. Preferably, R is the same in Formulae (X1) and (X2) as in Formulae (Q1) and (Q2). However, it is possible to convert one R moiety to another, for instance exchange a methyl group for a cyclohexyl group, whilst maintaining the chirality by methods known in organic chemistry (e.g. Houben-Weyl, Methods of organic chemistry), in which case R in Formulae (Q1) and (Q2). may be referred to as R' for the sake of clarity.

Preferably, the method of preparing the enantiomerically pure or enantiomerically enriched compound according to Formula (Q1) or Formula (Q2) as set out above further comprises (a) reacting (i) the optically active compound according to Formula (X1) or (iii) the mixture of compounds according to Formula (X1) and Formula (X2), in which mixture the compound according to Formula (X1) is present in excess, with a compound Y—CO—$CH_2$—X, wherein Y is F, Cl or Br or —O—CO-alkyl and X is F, Cl or Br, most preferably with chloroacetyl chloride (Cl—C(=O)—$CH_2$Cl), to give the compound according to Formula (Q1);

or (b) reacting the optically active compound according to the Formula (X2) or (iii) the mixture of compounds according to Formula (X1) and Formula (X2), in which mixture the compound according to Formula (X2) is present in excess, with a compound Y—CO—$CH_2$—X, wherein Y is F, Cl or Br or —O—CO-alkyl and X is F, Cl or Br, most preferably with chloroacetyl chloride (Cl—C(=O)—$CH_2$Cl), to give the compound according to Formula (Q2).

In said method, R is the same in Formulae (X1) and (X2) as in Formulae (Q1) and (Q2).

In the moiety "—O—CO-alkyl", alkyl encompasses an alkyl group having from one to six carbon atoms or cycloalkyl having from four to six ring C atoms.

As evident from the above, in the reaction of the compound of either Formula (X1) or (X2) with compound Y—CO—$CH_2$—X, the stereochemistry/chirality is maintained such that the resulting product (Q1) or (Q2) has the same configuration on the respective ring C-atom.

Most preferably, of course, the above methods are used for preparing enantiomerically pure or enantiomerically enriched (R)-Praziquantel:

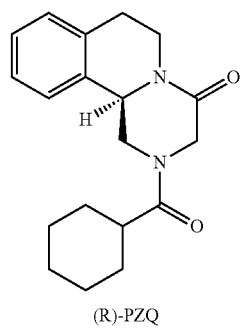 [SMILES: O=C(C1CCCCC1)N1CC(=O)N2CCc3ccccc3[C@@H]2C1]

(R)-PZQ in which case R is cyclohexl in the compounds according to Formula (X1) and (Q1) and in which case the respective steps (a) are employed. Thus in a preferred embodiment, the present invention provides a method of preparing enantiomerically pure or enantiomerically enriched (R)-Praziquantel comprising the method as described above for compounds (Q1) and (Q2), using the optically active compound according to Formula (X1) or (iii) the mixture of compounds according to Formula (X1) and Formula (X2), in which mixture the compound according to Formula (X1) is present in excess and wherein R is cyclohexyl in the compound according to Formulae (X1) and (Q1).

Expressed differently, the present invention provides a method of preparing enantiomerically pure or at least enantiomerically enriched (R)-Praziquantel

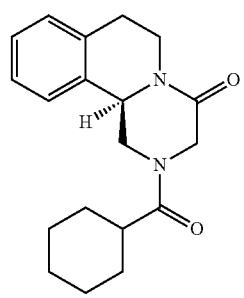 [SMILES: O=C(C1CCCCC1)N1CC(=O)N2CCc3ccccc3[C@@H]2C1]

comprising:

preparing (i) the optically active compound according to the Formula (X1) or (iii) the mixture of compounds according to Formula (X1) and Formula (X2), in which mixture the compound according to Formula (X1) is present in excess, and wherein R is cyclohexyl, according to the method of the present invention as set out above.

In analogy to what has been set out before, in preferred embodiments, the method of preparing (R)-Praziquantel further comprises reacting (i) the optically active compound according to Formula (X1) or (iii) the mixture of compounds according to Formula (X1) and Formula (X2), in which mixture the compound according to Formula (X1) is present in excess, with a compound Y—CO—$CH_2$—X, wherein Y is F, Cl or Br or —O—CO-alkyl and X is F, Cl or Br, most preferably with chloroacetyl chloride (Cl—C(=O)—CH₂Cl), to yield enantiomerically pure or at least enantiomerically enriched (R)-Praziquantel.

The cyclization reaction using Y—CO—CH₂—X, and in particular chloroacetyl chloride (Cl—C(=O)—CH₂Cl) as such is known from the prior art. For instance, the reaction is described as a two-step process in the conversion of a racemic mixture of compounds according to Formulae (X1) and (X2) to racemic Praziquantel in DE 2504250, which is incorporated by reference herein in its entirety. A reaction scheme starting from a compound of Formula (X1) involving a one-step reaction with chloroacetyl chloride (Cl—C(=O)—CH₂Cl) has been previously described, amongst others, by Sergovskaya and Chernyak (1991), as reproduced by Roszkowski, P. et al. in Tetrahedron: Asymmetry 17 (2006) 1415-1419, which is equally incorporated by reference herein in its entirety. Said reaction scheme involves reacting the compound of Formula (X1) with chloroacetyl chloride under Schotten-Baumann conditions, such as in a mixture of dichloromethane and 50% (aq) NaOH in the presence of TEBA chloride (benzyltriethylammonium chloride).

While the preparation of Praziquantel, and in particular (R)-Praziquantel is at the center of the present invention, analogues thereof are equally considered useful, either in their own right as pharmaceutical agents, or as interesting intermediate compounds.

For the purpose of the present invention "enantiomerically pure" shall mean that one enantiomer is present in an enantiomeric purity of at least 95% ee and preferably at least 98% ee, with ee representing enantiomeric excess as per the usual definition:

ee=[(|m₁−m₂|)/(m1+m2)]*100% with m₁ and m₂ being the masses of enantiomers 1 and 2, respectively. The term "enantiomerically enriched", as used herein, shall refer to a mixture of the two enantiomers, wherein the ratio of enantiomers is more than 50:50 (corresponding to ee>0%), preferably at least 55:45 (ee≥10%), at least 60 to 40 (ee≥20%) or 70:30 (ee≥40%) or 80:20 (ee≥60%) or 90:10 (ee≥80%), but less than 97.5:2.5 (ee<95%). In a "racemic mixture", the enantiomeric ratio is 50:50 and thus the enantiomeric excess ee equal to zero. The term "mixture of enantiomers" includes racemic mixtures as well as mixtures of any other ratio or enantiomers between 50:50 and <100:0.

In a preferred alternative, the present invention provides a method of preparing an enantiomerically pure or enantiomerically enriched compound according to Formula (Q1) or Formula (Q2)

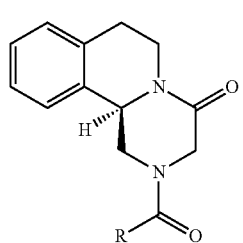

(Q1)

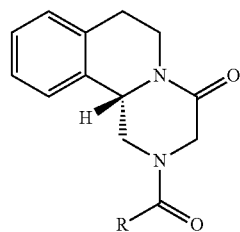

(Q2)

comprising preparing a mixture of compounds according to Formula (X1) or Formula (X2) in accordance with the method of the present invention, i.e. starting from compound Y, separating the compound according to Formula (X1) from the compound according to Formula (X2), and reacting (a) the compound according to Formula (X1) with a compound Y—CO—CH₂—X, wherein Y is F, Cl or Br or —O—CO-alkyl and X is F, Cl or Br, most preferably with chloroacetyl chloride (Cl—C(=O)—CH₂Cl, to obtain the enantiomerically pure or at least enantiomerically enriched compound according to Formula (Q1);

or (b) the compound according to Formula (X2) with a compound Y—CO—CH₂—X, wherein Y is F, Cl or Br or —O—CO-alkyl and X is F, Cl or Br, most preferably with chloroacetyl chloride (Cl—C(=O)—CH₂Cl, to obtain the enantiomerically pure or at least enantiomerically enriched compound according to Formula (Q2).

Thus, in an alternative embodiment, a method of preparing enantiomerically pure or enantiomerically enriched (R)-Praziquantel comprises:

preparing a mixture of compounds according to Formula (X1) and Formula (X2), wherein R is cyclohexyl, according to the method of the invention as set out above, separating the compound according to Formula (X1) from the compound according to Formula (X2), and reacting the compound according to Formula (X1) with Y—CO—CH₂—X, with X and Y as above, most preferably chloroacetyl chloride (Cl—C(=O)—CH₂Cl) to yield the enantiomerically pure or enantiomerically enriched (R)-Praziquantel.

Separating the compound according to Formula (X1) from the compound according to Formula (X2) or vice versa may involve any suitable known method of chiral resolution, for instance chiral resolution via diastereomeric salt formation or chiral chromatography. Diastereomeric salt formation may involve known suitable optically active acids, such as the (+)- and (−)-forms of tartaric acid, dibenzoyltartaric acid, diacetyltartaric acid, dipivaloyltartaric acid, mandelic acid, malic acid, lactic acid, 2-phenyl-butanoic acid, campheric acid, β-camphorsulfonic acid, dinitrodiphenic acid or quinic acid. Diastereomeric salts are then crystallized from a suitable solvent, such as ethanol, and the desired enantiomer is then isolated after release of the diastereomeric salt under suitable conditions, such as either basic or acidic conditions, and typically extraction with a suitable solvent, such as dichloromethane or chloroform.

A preferred example of separating the compounds of Formulae (X1) and (X2) to yield compound (X1) in enantiomerically pure or enantiomerically enriched form is chiral resolution via formation of a diastereomeric salt, preferably with D-(−)-tartaric acid, preferably in combination with crystallization from ethanol. The diastereomeric salt is typically released under basic conditions, for instance using sodium hydroxide, followed by extraction, for instance with dichloromethane, and evaporation in vacuo.

It is possible to recycle the remains of the chiral separation, i.e. the undesired enantiomer, possibly in admixture with some of the desired enantiomer, by dehydrogenation and subsequent hydrogenation, as illustrated by the following reaction scheme, which represents a further aspect of the present invention:

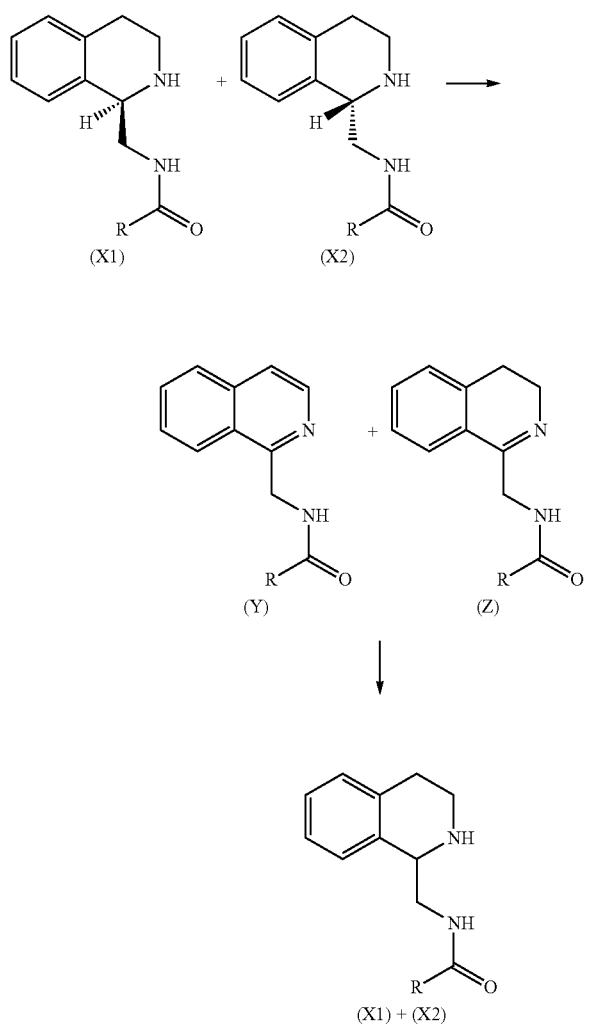

The compounds of Formulae (X1) and (X2) are subjected to a dehydrogenation step, for instance using ethylene and Pd—C as a catalyst, to yield a mixture of compound (Y) and its dehydro-derivative (Z). Said mixture may then be subjected to a hydrogenation reaction, such as a non-selective hydrogenation reaction, for instance using hydrogen and Pt—C as a catalyst, as mentioned above, to yield a mixture, typically racemic mixture, of compounds of Formulae (X1) and (X2), which may be subjected to another step of chiral resolution, for instance.

Accordingly, in a further aspect, the present invention provides a method of preparing a mixture of an optically active compound according to Formula (X1) and an optically active compound according to Formula (X2):

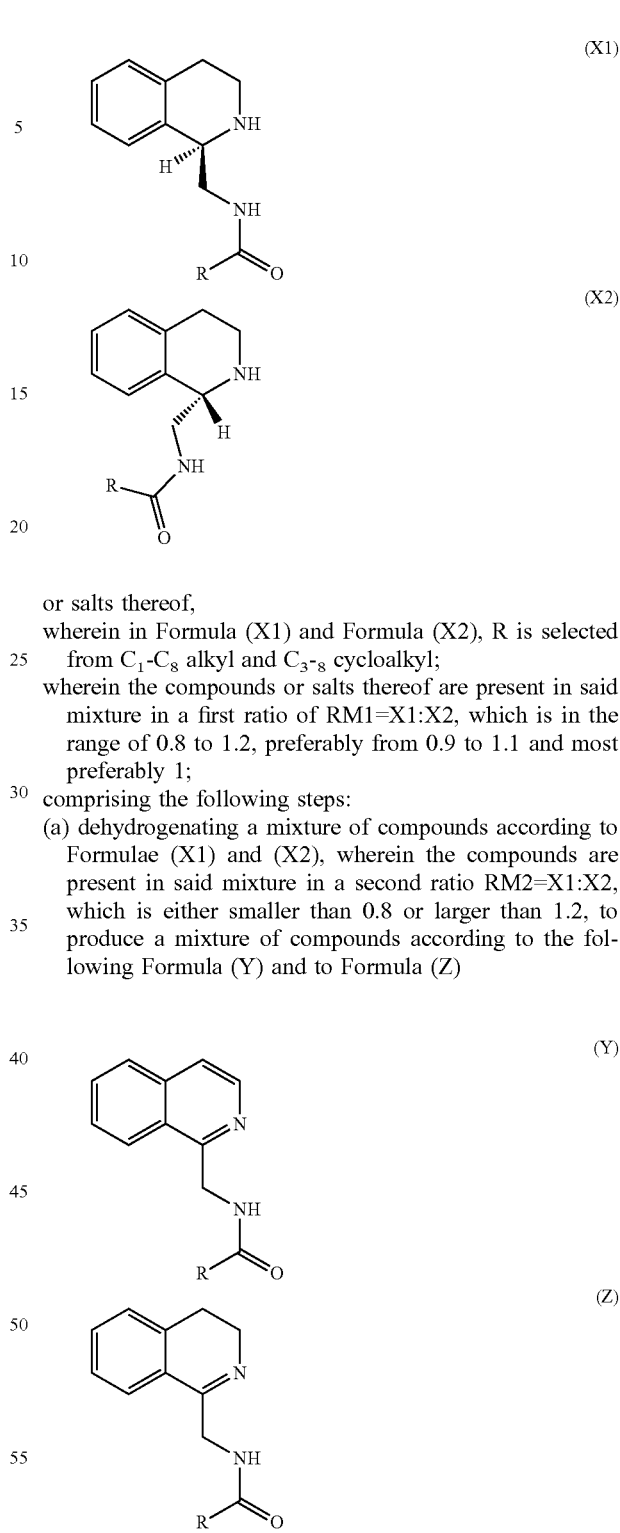

or salts thereof,
wherein in Formula (X1) and Formula (X2), R is selected from $C_1$-$C_8$ alkyl and $C_{3-8}$ cycloalkyl;
wherein the compounds or salts thereof are present in said mixture in a first ratio of RM1=X1:X2, which is in the range of 0.8 to 1.2, preferably from 0.9 to 1.1 and most preferably 1;
comprising the following steps:
(a) dehydrogenating a mixture of compounds according to Formulae (X1) and (X2), wherein the compounds are present in said mixture in a second ratio RM2=X1:X2, which is either smaller than 0.8 or larger than 1.2, to produce a mixture of compounds according to the following Formula (Y) and to Formula (Z)

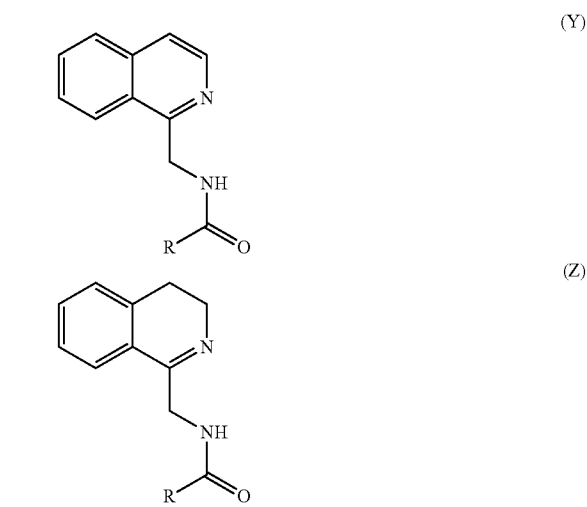

or salts thereof
(b) hydrogenating said mixture of compounds according to Formula (Y) and to Formula (Z) or salts thereof to obtain the mixture of compounds of Formulae (X1) and (X2) or salts thereof in the first ratio RM1.

As evident from the ratios of compounds of Formulae (X1) and (X2), it is the purpose of said reaction to decrease the amount of undesired compound, be it compound of Formula (X1) or (X2) in a mixture, and to ideally arrive at a racemic mixture, which has a more favourable amount of the desired compound and can therefore be more suitably subjected to a (further) chiral resolution step.

Typically, the mixture of compounds according to Formulae (X1) and (X2) or salts thereof in the second ratio RM2 will be the undesired remains of a chiral resolution, i.e. said mixture would then be prepared by separation of a mixture of compounds according to Formulae (X1) and (X2), either as a product or as a side-product. Less typically, the mixture of compounds according to Formulae (X1) and (X2) or salts thereof in the second ratio RM2 can be the result of an asymmetric hyrogenation step of a compound according to Formula (Y) in accordance with the method according to the invention, particularly if said asymmetry hydrogenation leads to an excess of undesired enantiomer.

The salt can be any salt form of the compound that can be suitably subjected to a dehydrogenation and hydrogenation step. If the initial mixture is the result, or remains, of a chiral resolution step, the salt may be a diastereomeric salt, i.e. a salt of the respective compound with a diastereomeric counter-ion.

The two steps can be carried out without isolation of intermediate products. In the alternative, it is possible to isolate the intermediate products, i.e. the compounds of Formula (Y) and (Z).

Under a further aspect, the present invention relates to a compound according to the following Formula (Y1)

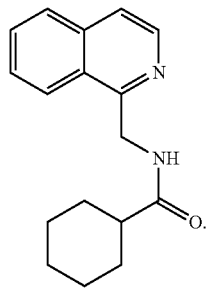

(Y1)

This compound is regarded as a key intermediate in the syntheses of the present invention, and in particular, allows preparing (R)-Praziquantel in a stereoselective manner.

The present invention thus further provides the use of a compound of Formula (Y1) for the preparation of (R)-Praziquantel, or, expressed differently, a method for preparing (R)-Praziquantel using compound (Y1) as a starting or intermediate compound.

More generally, the present invention further provides use of compounds of Formula (Y)

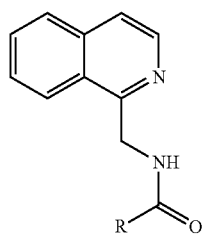

(Y)

for the preparation of
(i) an optically active compound according to the following Formula (X1)

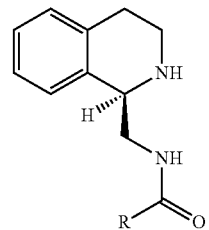

(X1)

or
(ii) an optically active compound according to the following Formula (X2)

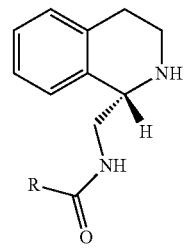

(X2)

or
(iii) a mixture of the two,
with R (in (Y) as well as (X1) and (X2)) being selected from $C_1$-$C_8$ alkyl, $C_3$-$C_8$ cycloalkyl, and optionally substituted aryl, most preferably cyclohexyl.

The present invention further provides a method of preparing a compound of Formula (Y1)

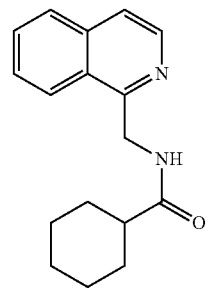

(Y1)

comprising reacting [(isoquinolin-1-yl)-methyl]-amine

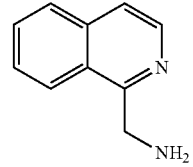 [SMILES: NCc1nccc2ccccc12]

with a cyclohexane carboxylic acid based acylating agent. There are different ways of coupling the cyclohexane carboxy derivative with the amine, for instance by formation of an intermediate acylating agent and isolation, then aminolysis; formation of a reactive acylating agent in a separate step, followed by immediate treatment with the amine; or generation of the acylating agent in situ from the cyclohexane carboxylic acid in the presence of the amine, by the addition of an activating or coupling agent.

The cyclohexane carboxylic acid based acylating agent can be, for instance, cyclohexane carboxylic acid in the presence of an activating or coupling agent, or a cyclohexane carboxylic acid derivative preferably selected from cyclohexane carboxylic acid chloride, cyclohexane carboxylic acid anhydride, and mixed anhydride of cyclohexane carboxylic acid and pivalic acid.

The mixed anhydride of cyclohexane carboxylic acid and pivalic acid can be prepared in situ, for instance, from cyclohexane carboxylic acid and pivaloylchloride in the presence of a tertiary amine as a base. The reaction with cyclohexane carboxylic acid itself involves the use of an activating or coupling agent or both. The formation of amides starting from amines is well established. Further examples of suitable reactants or reaction conditions, including condensing agents and activators, can be found in Montalbette C.A.G.N. et al., "Amide bond formation and peptide coupling", Terahedron 61 (2005) pp. 10827-10852, the entire contents of which are incorporated herein by reference.

The reaction with cyclohexane carboxylic acid chloride is preferred and preferably carried out under basic conditions, for instance in a solvent system comprising THF and a basic aqueous solution, for instance a NaOH aqueous solution. Other suitable solvents include DCM, dioxane, toluene and methyl-tert.-butyl ether, for instance.

Generally, the starting materials for the preparation of compounds of the present invention as well as the catalysts can be prepared by methods as described in the following Examples or by methods known per se, as described in the literature of synthetic organic chemistry (e.g. Houben-Weil, Methods of Organic Chemistry) and known to the skilled artisan, or can be obtained commercially.

The compounds and processes of the present invention are illustrated by the following Examples, which shall not be regarded as limiting the present invention. Unless indicated otherwise, variables, if any, shall have the same meaning as described above.

Abbreviations:
ee enantiomeric access
HPLC High Performance Liquid Chromatography
J Coupling constant
m Multiplet
mL Milliliter
mp Melting Point
MS Mass Spectrometry
(S)-PZQ (S)-Praziquantel
(R)-PZQ (R)-Praziquantel
RT Room Temperature
Temp Temperature
[S] Substrate concentration
S Substrate
C Catalyst
s Singulet
t Triplet
THF Tetrahydrofuran
[Ir(COD)Cl]$_2$ Cyclooctadiene iridium chloride dimer
3,5-Me$_2$-Ph 3,5-Dimethylphenyl (Xylyl)
Ph Phenyl
t-Bu Tert. butyl
3,5-F-Ph 3,5-Difluorophenyl
Me$_2$-Ph Dimethylphenyl (Xylyl)
Me Methyl
Et Ethyl
iPr Isopropyl
Bn Benzyl
c-Hex Cyclohexyl
TEBAC Benzyltriethylammonium chloride
Me-THF 2-Methyltetrahydrofuran
IPA Isopropyl alcohol
DCE Dichloroethane
DCM Dichloromethane
EtOAc Ethylacetate

EXAMPLE 1

Synthesis of (R)-Praziquantel: Route 1

Step 1: Preparation of isoquinaldonitrile (2)

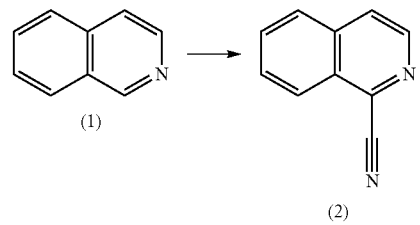 [SMILES: c1ccc2cnccc2c1 ; N#Cc1nccc2ccccc12]

Isoquinaldonitrile (2) is commercially available and can be prepared from isoquinoline (1) according to reported procedures, such as the following: J. M. Wefer, A. Catala, F. D. Popp, Chem. Ind. (London) 1965, 140-141; J. M. Wefer, A. Catala, F. D. Popp, J. Org. Chem. 1965, 30, 3075-3077; M. D. Rozwadowska, D. Brozda, Can. J. Chem. 1980, 58, 1239-1242 and D. L. Boger, C. E. Brotherton, J. S. Panek, D. Yohannes, J. Org. Chem. 1984, 49, 4056-4058, which are incorporated herein by reference in their entirety.

Step 2: Preparation of
[(Isoquinolin-1-yl)-methyl]amine (3)

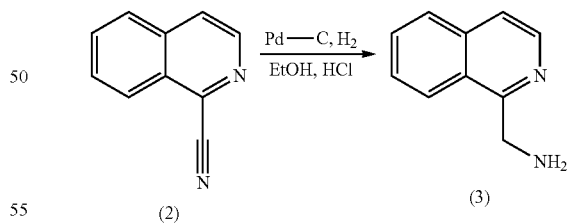

18 g (0.117 mol) Isoquinaldonitrile (2) are dissolved in ethanol (250 g) and 18.6 g hydrochloric acid (32%) under stirring at room temperature. After addition of 7.8 g wet palladium-charcoal (5%), atmospheric pressure of hydrogen is applied for 17 h. Afterwards, the resulting mixture is filtered over celite and the filtrate concentrated in vacuo. The residue is then dissolved in a biphasic mixture of dichloromethane (150 g) and 32%-NaOH aqueous solution (55 g). The phases are separated and the aqueous layer is extracted three times with dichloromethane (200 g). The combined organic layers are finally evaporated affording [(isoquinolin-1-yl)-methyl]-amine (3) as a light brown solid (20.4 g, 90% yield).

Characterization of
[(Isoquinolin-1-yl)-methyl]-amine $C_{10}H_{10}N_2$ (158.20 g·mol$^{-1}$), mp. 211-212° C.
$^1$H NMR (d$^6$-DMSO): 8.47 (d, J=5 Hz, 1H$_{arom}$), 8.26 (d, J=8 Hz, 1H$_{arom}$), 7.96 (d, J=8 Hz, 1H$_{arom}$), 7.77 (t, J=6 Hz, 1H$_{arom}$), 7.71 (d, J=5 Hz, 1H$_{arom}$), 7.67 (t, J=6 Hz, 1H$_{arom}$), 4.39 (s, 2H), 2.70 (bs, NH$_2$)

Step 3: Preparation of N-(1-isoquinolin-1-yl-methyl)-cyclohexane carboxylic acid-amide (4)

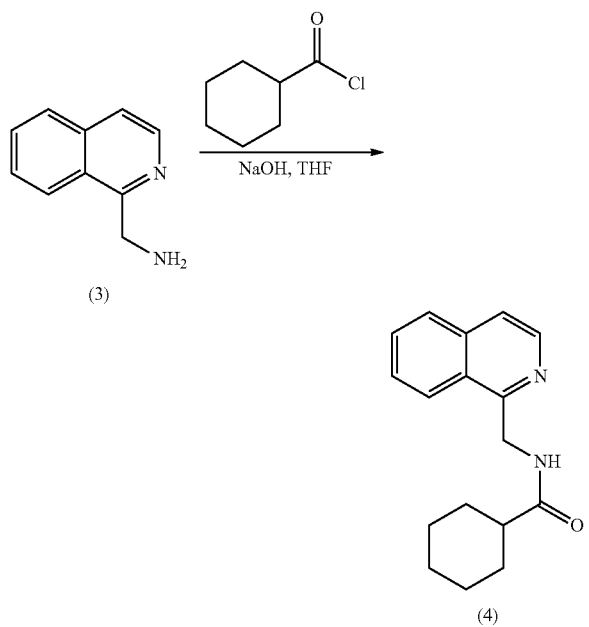

58.9 g (0.372 mol) [(Isoquinolin-1-yl)-methyl]amine (3) are dissolved in THF (250 g) under stirring at room temperature. 51.2 g (0.410 mol) of 32%-NaOH aqueous solution and water (150 g) are added. The mixture is cooled down to 10° C. before dropwise addition of a solution of 60 g (0.410 mol) cyclohexane carboxylic-acid chloride in THF (50 g) within 2.5 h at 10-15° C. The resulting biphasic mixture is stirred at room temperature for 2 h before addition of 2N HCl (191 g). 300 g Methyl-THF and 350 g water are added to enable phase separation, the aqueous layer is separated and the organic phase is extracted twice with 1N HCl (190 g). The aqueous phases are combined, washed with methyl-THF (200 g) and then neutralized with 32%-NaOH aqueous solution (106 g). Methyl-THF (200 g) is added, the phases are separated, the aqueous phase is extracted twice with methyl-THF (200 g), the combined organic phases are finally evaporated and the crude solid residue is recrystallized from ethyl acetate affording N-(1-isoquinolin-1-yl-methyl)-cyclohexane carboxylic acid-amide (4) as a white to light yellow solid after drying (69.9 g, 70% yield). Second crop crystals can be isolated through recrystallization of mother liquor residue from ethyl acetate (15 g, total yield 85%).

Characterization of
N-(1-isoquinolin-1-yl-methyl)-cyclohexane carboxylic acid-amide $C_{17}H_{20}N_2O$ (268.36 g·mol$^{-1}$), mp. 126-128° C.
$^1$H NMR (CDCl$_3$): 8.44 (d, J=6 Hz, 1H$_{arom}$), 8.12 (ddd, J=9 Hz, J=3 Hz, J=0.5 Hz, 1H$_{arom}$), 7.85 (dt, J=9 Hz, J=0.5 Hz, 1H$_{arom}$), 7.59-7.75 (m, 3H$_{arom}$), 7.55 (bs, NH), 5.06 (d, J=6 Hz, 2H), 2.31 (tt, J=9 Hz, J=3 Hz, 1H), 1.96-2.03 (m, 2H), 1.80-1.87 (m, 2H), 1.67-1.73 (m, 1H), 1.50-1.57 (m, 2H), 1.22-1.39 (m, 3H)
$^{13}$C NMR (CDCl$_3$): 176.2 (s, 1C=O), 154.8 (s, 1qC$_{arom}$), 140.9 (s, 1C$_{arom}$)) 136.0 (s, 1qC$_{arom}$), 130.4 (s, 1C$_{arom}$), 127.8 (s, 1C$_{arom}$), 127.3 (s, 1C$_{arom}$), 125.9 (s, 1qC$_{arom}$), 123.9 (s, 1C$_{arom}$), 120.4 (s, 1C$_{arom}$), 45.6 (s, CH), 41.9 (s, 1CH$_2$), 29.8 (s, 2CH$_2$), 25.9 (s, 3CH$_2$)
MS (EI) m/z (%): 268 (19) [M], 250 (18), 221 (10), 195 (19), 185 (27), 182 (15), 157 (100), 142 (36), 130 (11), 115 (28), 77 (4)

Step 4: Preparation of [(R)-1-(1,2,3,4-tetrahydro-isoquinolin-1-ylmethyl)]-cyclohexanecarboxylic acid-amide (5(R))

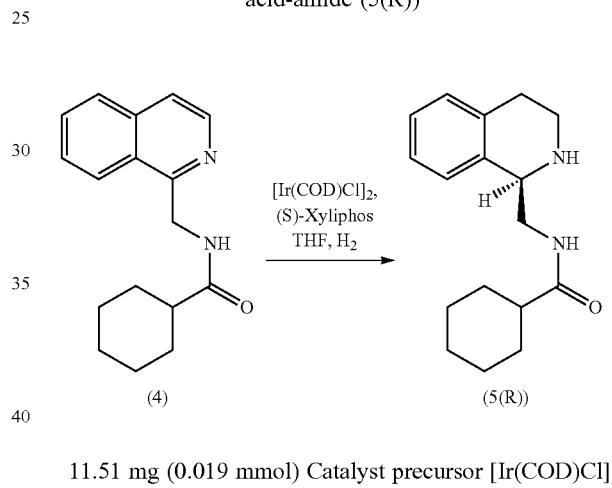

11.51 mg (0.019 mmol) Catalyst precursor [Ir(COD)Cl]$_2$ and 26.17 mg (0.041 mmol) (S)-Xyliphos are mixed together and dissolved in THF (5 g) in an inertized glove box. 0.2 g (0.75 mmol) N-(1-isoquinolin-1-yl-methyl)-cyclohexane carboxylic acid-amide (4) are dissolved in THF (25 g) in an autoclave under nitrogen at room temperature. The catalyst solution is added with a syringe to the autoclave before applying a hydrogen pressure of 100 bar and heating up to 75° C. The pressure rose up to 110 bar over the 24 h reaction time affording a conversion of 56% for the targeted [(R)-1-(1,2,3,4-tetrahydro-isoquinolin-1-ylmethyl)]-cyclohexanecarboxylic acid-amide (5(R)), which is also referred to as (R)-PZQ-Carboxamide herein, with an enantioselectivity of ee=64%. The reaction mixture can finally be evaporated, purified through chromatography and finally crystallized from n-heptane/ethanol to improve the ee of (R)-PZQ-Carboxamide (5(R)) up to 96%.

Characterization of [(R)-1-(1,2,3,4-tetrahydro-iso-quinolin-1-ylmethyl)]-cyclo-hexane -carboxylic acid-amide $C_{17}H_{24}N_2O$ (272.39 g·mol$^{-1}$), mp. 110-112° C.
NMR data were in full accordance with the data of the racemate (see below).

21
Step 5: Preparation of (R)-Praziquantel

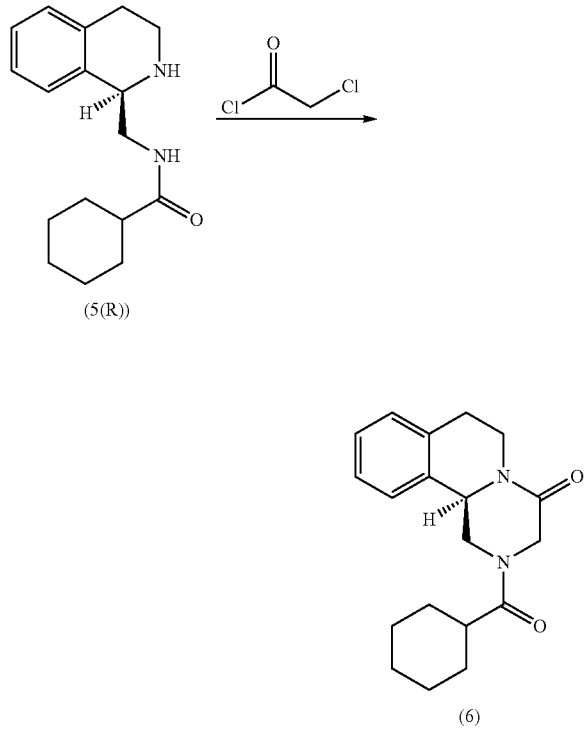

(5(R))

(R)-Praziquantel ((R)-PZQ) (6) can be prepared from [(R)-1-(1,2,3,4-tetrahydro-isoquinolin-1-ylmethyl)]-cyclohexanecarboxylic acid-amide (5(R)) ((R)-PZQ-Carboxamide) through cyclization with chloro-acetyl chloride according to known procedures, such as the procedure described by Sergovskaya and Chernyak (1991), as reproduced by Roszkowski, P. et al. in Tetrahedron: Asymmetry 17 (2006) 1415-1419: To a stirred solution of amine (1R)-7 [in the present case (5(R))] (110 mg, 0.39 mmol) in 1.0 mL $CH_2Cl_2$, a solution of 50% NaOH (0.12 mL, 1.33 mmol) was added, followed by the addition of a solution of chloroacetyl chloride (0.034 mL, 0.43 mmol) in 0.15 mL of $CH_2Cl_2$. After 0.5 h, TEBAC (9 mg, 0.04 mmol) was added and the mixture was heated and stirred for 2 h at reflux. After that time, a portion of 3 mL of water was added and the mixture extracted with $CH_2Cl_2$ (2×3 mL). The organic phase was washed with water (2×2 mL), 5% HCl (2 mL), again with water (2 mL) and dried over Na2SO4. After evaporation of the solvent, the residue was purified with column chromatography on silica gel using chloroform/methanol 0-0.3% MeOH as a solvent system to afford 93 mg (77%) of (1R)-(−)-8 [in the present case (R)-PZQ].

Characterization of (R)-PZ $C_{19}H_{24}N_2O_2$ (312.42 g·mol$^{-1}$), mp. 110-111° C.
Analytical data already known and described.

22
EXAMPLE 2

Synthesis of (R)-Praziquantel: Route 2

Steps 1 to 3 in the Preparation of N-(1-isoquinolin-1-yl-methyl)-cyclohexane carboxylic acid-amide (4) are the Same as in Route 1

Step 4: Preparation of N-(1,2,3,4-tetrahydro-isoquinolin-1-ylmethyl)-cyclohexanecarboxylic acid-amide (5)

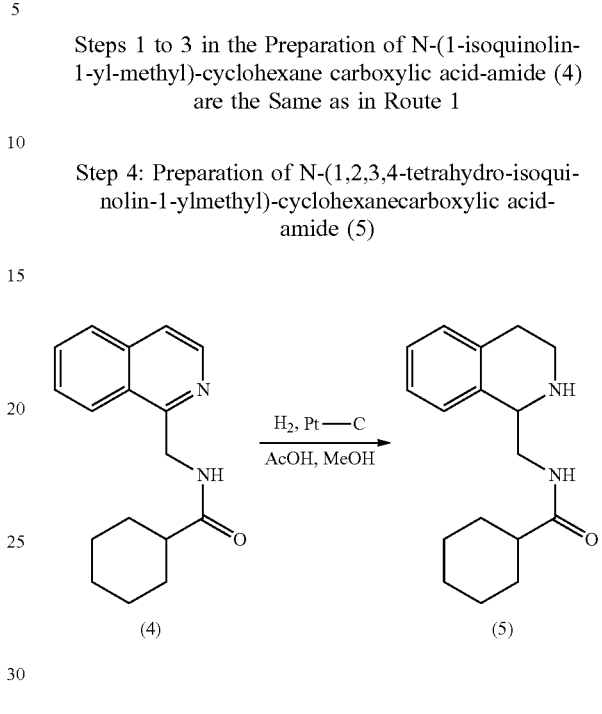

21 g (0.078 mol) N-(1-isoquinolin-1-yl-methyl)-cyclohexane carboxylic acid-amide (4) are dissolved in methanol (MeOH, 145 g) and glacial acetic acid (AcOH, 2.18 g, 0.036 mol) under stirring at room temperature. After addition of 11.8 g wet platinum on activated charcoal (5%) (Pt—C), a hydrogen ($H_2$) pressure of 2.6 bar and a temperature of 35° C. are applied for 16 h, the mixture is afterwards filtered over celite and the filtrate concentrated in vacuo. The residue is taken up in dichloromethane (200 g), washed with NaOH (5%) until a pH of 12-13 has been reached. After phase separation, the aqueous layer is extracted with dichloromethane (90 g), the combined organic phases are washed three times with water (75 g) reaching a pH of 7 and finally evaporated. The residue is recrystallized from ethyl acetate affording a racemic mixture of N-(1,2,3,4-tetrahydro-isoquinolin-1-ylmethyl)-cyclohexanecarboxylic acid-amide (5) as light yellowish crystals after drying (14.5 g, 68% yield).

Characterization of N-(1,2,3,4-tetrahydro-isoquinolin-1-ylmethyl)-cyclohexane-carboxylic acid-amide:

$C_{17}H_{24}N_2O$ (272.39 g·mol$^{-1}$), mp. 106-108° C.

$^1$H NMR (CDCl$_3$): 7.12-7.03 (m, 3H$_{arom}$), 7.03-6.93 (m, 1H$_{arom}$), 6.27 (t, J=6 Hz, NH), 3.97 (dd, J=9 Hz, J=5 Hz, 1H), 3.71-3.63 (m, 1H), 3.30-3.20 (m, 1H), 3.09-3.00 (m, 1H), 2.98-2.89 (m, 1H), 2.70-2.63 (m, 2H), 2.05-1.94 (m, 2H), 1.78-1.53 (m, 5H), 1.41-1.25 (m, 2H), 1.25-1.07 (m, 3H)

$^{13}$C NMR (CDCl$_3$): 176.4 (s, 1C=O), 136.0 (s, 1qC$_{arom}$), 135.4 (s, 1C$_{arom}$)) 129.3 (s, 1C$_{arom}$)) 126.5 (s, 1C$_{arom}$), 126.4 (s, 1C$_{arom}$), 126.1 (s, 1C$_{arom}$), 55.0 (s, 1CHN), 45.5 (s, 1CH), 43.3 (s, 1CH$_2$), 39.8 (s, 1CH$_2$), 29.7 (s, 2CH$_2$), 29.6 (s, 1CH$_2$), 25.7 (s, 3CH$_2$)

MS (EI) m/z (%): 273 (100) [M+H]$^+$

Step 5: Chiral Resolution of racemic N-(1,2,3,4-tetrahydro-isoquinolin-1-ylmethyl)-cyclohexanecarboxylic acid-amide (5)

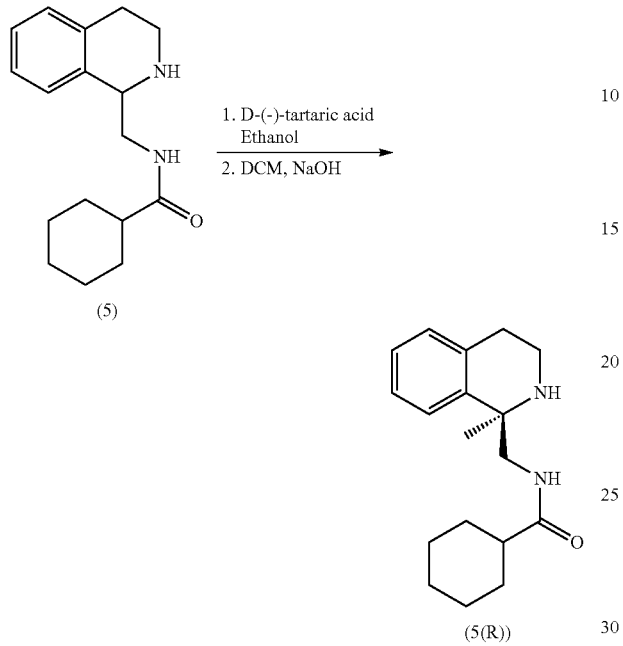

Racemic N-(1,2,3,4-tetrahydro-isoquinolin-1-ylmethyl)-cyclohexanecarboxylic acid-amide (5) can be resolved via formation and crystallization of diastereomeric salts with D-(−)-tartaric acid from ethanol. After release of the diastereomeric salt under basic conditions (NaOH), extractions with dichloromethane and evaporation in vacuo, [(R)-1-(1,2,3,4-tetrahydro-isoquinolin-1-ylmethyl)]-cyclo-hexane-carboxylic acid-amide (5(R) is obtained as a white solid with 60% yield and 96% ee.

A further suitable procedure is described, for instance, in DE2504250 (Example 91): A solution of 16.5 g (D)-(−)-tartaric acid in 300 mL methanol is added to a solution of 21.7 g racemic N-(1,2,3,4-tetrahydro-isoquinolin-1-ylmethyl)-cyclohexanecarboxylic acid-amide (prepared differently in DE2504250) in 300 mL methanol. The solvent is distilled off, and the residue from ethanol recrystallized until the melting point has increased to about 207° C. The salt is dissolved in water, the solution rendered alkaline and then extracted with chloroform or dichloromethane. After drying over magnesium sulphate and distilling off the solvent, [(R)-1-(1,2,3,4-tetrahydro-isoquinolin-1-ylmethyl)]-cyclohexane-carboxylic acid-amide (5(R) is obtained.

Characterization of [(R)-1-(1,2,3,4-tetrahydro-isoquinolin-1-ylmethyl)]-cyclo-hexane -carboxylic acid-amide $C_{17}H_{24}N_2O$ (272.39 g·mol$^{-1}$), mp. 110-112° C.

Step 6 (optional): Recycling of [(S)-1-(1,2,3,4-tetrahydro-isoquinolin-1-ylmethyl)]-cyclohexane-carboxylic acid-amide

[(S)-1-(1,2,3,4-tetrahydro-isoquinolin-1-ylmethyl)]-cyclohexane-carboxylic acid-amide or mixtures of [(R)-1-(1,2,3,4-tetrahydro-isoquinolin-1-ylmethyl)]-cyclohexane-carboxylic acid-amide and [(S)-1-(1,2,3,4-tetrahydro-isoquinolin-1-ylmethyl)]-cyclohexane-carboxylic acid-amide with an excess of the (S)-configured compound can be recycled via dehydrogenation and rehydrogenation to produce a racemic mixture of the compounds for further chiral resolution as follows:

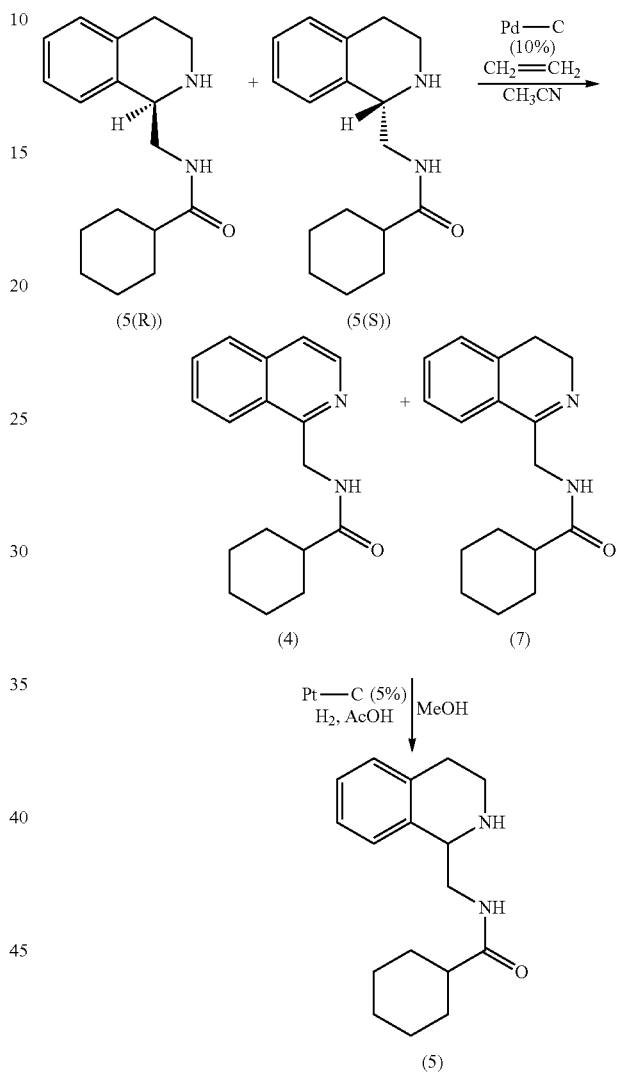

The mother and wash liquor from the chiral resolution step 5 described above are evaporated, treated with dichloromethane and aqueous sodium hydroxide. After extractions of the aqueous layer with dichloromethane, the combined organic layers are evaporated in vacuo affording a mixture of and [(S)-1-(1,2,3,4-tetrahydro-isoquinolin-1-ylmethyl)]-cyclohexane-carboxylic acid-amide and some residual [(R)-1-(1,2,3,4-tetrahydro-isoquinolin-1-ylmethyl)]-cyclohexane-carboxylic acid-amide.

5 g (0.018 mol) of the evaporation residue are dissolved in acetonitrile (30 g) and 2.5 g Pd—C(10%) are added before applying an ethylene pressure of 10 bar, and subsequently heating up to 100° C. for 18 h, whereas the internal pressure in the autoclave reached a maximum of 20 bar. The mixture is finally filtered over celite, the catalyst washed with warm acetonitrile and the resulting filtrate concentrated in vacuo affording 4.5 g of a light brown solid containing a mixture of N-(1-isoquinolin-1-yl-methyl)-cyclohexane carboxylic acid-amide (4) (53.6%) and its dehydro-derivative (7) (44.3%).

This residual mixture is directly used for hydrogenation and dissolved in methanol (63 g) and acetic acid (0.178 g, 0.003 mol). After addition of 1.8 g (0.008 mol) wet platinum on activated charcoal (5%), a hydrogen pressure of 2.8 bar and a temperature of 36° C. are applied for 7 h, the mixture is afterwards filtered over celite and the filtrate concentrated in vacuo. The residue is taken up in dichloromethane (40 g), washed with NaOH (5%) until a pH of 12-13 has been reached. After phase separation the aqueous layer is extracted with dichloromethane (20 g), the combined organic phases are washed three times with water (30 g) reaching a pH of 7 and finally evaporated. The residue is recrystallized from ethyl acetate affording 1-(1,2,3,4-tetrahydro-isoquinolin-1-ylmethyl)]-cyclo-hexane-carboxylic acid-amide as light yellowish crystals after drying (2.92 g, 65% yield). This material can subsequently be used for a further step of chiral resolution.

Step 7: Preparation of (R)-Praziquantel (R)-Praziquantel ((R)-PZQ) (6) can be prepared from [(R)-1-(1,2,3,4-tetrahydro-isoquinolin-1-ylmethyl)]-cyclohexanecarboxylic acid-amide as described in Step 5 of EXAMPLE 1.

EXAMPLE 3

Synthesis of Racemic Praziquantel

Steps 1 to 4 are the Same as in EXAMPLE 2 (Route 2)

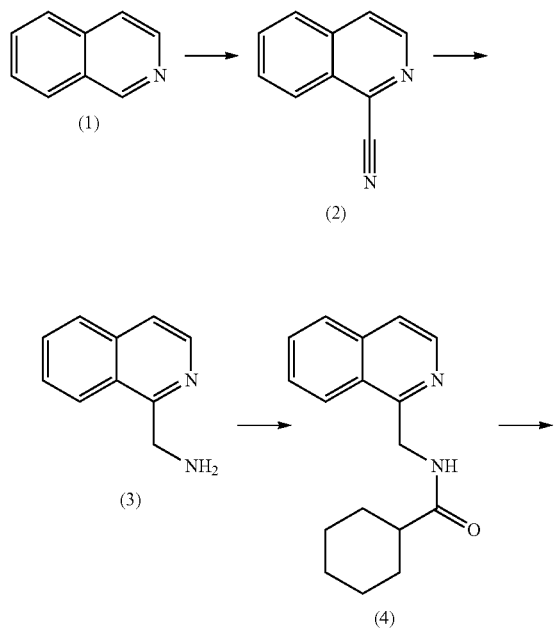

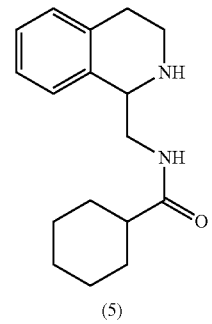

Step 5: Preparation of Racemic Praziquantel

Racemic Praziquantel (PZQ) is prepared from racemic 1-(1,2,3,4-tetrahydro-isoquinolin-1-ylmethyl)]-cyclohexanecarboxylic acid-amide in the same manner as described in Step 5 of EXAMPLE 1.

EXAMPLE 4

Synthesis Of [(S)-1-(1,2,3,4-tetrahydro-isoquinolin-1-ylmethyl)]-cyclohexanecarboxylic acid-amide Steps 1 and 2 are the Same as Steps 1 and 2 in EXAMPLES 1 to 3

Step 3: Preparation of N-Isoquinolin-1-yl-methyl-acetamide

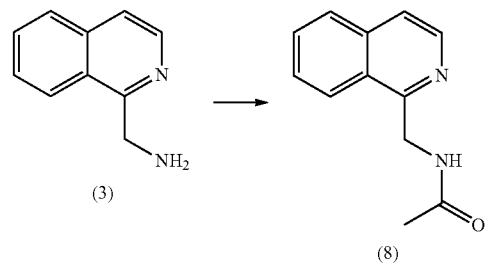

N-Isoquinolin-1-yl-methyl-acetamide (8) is synthesized by reacting [(Isoquinolin-1-yl)-methyl]-amine (3) with acetic acid-chloride in analogy to the preparation of N-(1-isoquinolin-1-yl-methyl)-cyclohexane carboxylic acid-amide (4) (Step 3 in EXAMPLE 1).

Characterization of N-Isoquinolin-1-yl-methyl-acetamide $C_{12}H_{12}N_2O$ (200.24 g·mol$^{-1}$), mp. 127.5-130.5° C.
$^1$H NMR (CDCl$_3$): 8.41 (d, J=6 Hz, 1H$_{arom}$), 8.10 (ddd, J=9 Hz, J=3 Hz, J=0.5 Hz, 1H$_{arom}$), 7.84 (dt, J=9 Hz, J=0.5 Hz, 1H$_{arom}$), 7.58-7.75 (m, 3H$_{arom}$), 7.55 (bs, NH), 5.05 (d, J=6 Hz, 2H), 2.16 (s, 3H)
$^{13}$C NMR (CDCl$_3$): 170.2 (s, 1C=O), 154.4 (s, 1qC$_{arom}$), 140.8 (s, 1C$_{arom}$), 135.9 (s, 1qC$_{arom}$), 130.4 (s, 1C$_{arom}$), 127.8 (s, 1C$_{arom}$), 127.3 (s, 1C$_{arom}$), 125.8 (s, 1qC$_{arom}$), 123.8 (s, 1C$_{arom}$), 120.5 (s, 1C$_{arom}$), 42.1 (s, 1CH$_2$), 23.3 (s, 1CH$_3$)

MS (EI) m/z (%): 200 (21) [M], 182 (34), 157 (100), 142 (18), 130 (17), 115 (16), 77 (9), 43 (8)

Step 4a: Preparation of [(S)-1-(1,2,3,4-tetrahydro-isoquinolin-1-ylmethyl)]-acetamide

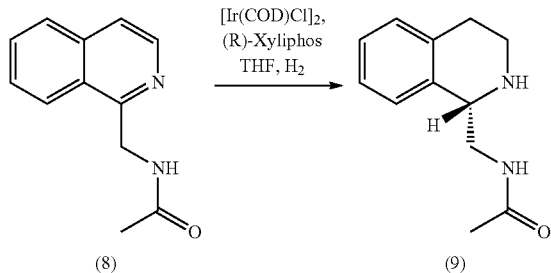

15.30 mg (0.025 mmol) catalyst precursor [Ir(COD)Cl]$_2$ and 34.73 mg (0.054 mmol) (R)-Xyliphos are mixed together and dissolved in THF (5 g) in an inertized glove box. 0.2 g (0.99 mmol) N-Isoquinolin-1-yl-methyl-acetamide (8) are dissolved in THF (25 g) in an autoclave under nitrogen at room temperature. The catalyst solution is added with a syringe to the autoclave before applying a hydrogen pressure of 100 bar and heating up to 100° C. The pressure rose up to 110 bar over the 17 h reaction time affording a conversion of 77.5% for the targeted [(S)-1-(1,2,3,4-tetrahydro-isoquinolin-1-ylmethyl)]-acetamide (9) with an enantioselectivity of ee=84%. The reaction mixture can finally be evaporated, purified through chromatography and finally crystallized to improve the ee of targeted [(S)-1-(1,2,3,4-tetrahydro-isoquinolin-1-ylmethyl)]-acetamide (9) up to 96%.

Characterization of [(S)-1-(1,2,3,4-tetrahydro-isoquinolin-1-ylmethyl)]-acetamide $C_{12}H_{16}N_2O$ (204.27 g·mol$^{-1}$), mp. 55° C.

Step 4b: Preparation of [(R)-1-(1,2,3,4-tetrahydro-isoquinolin-1-ylmethyl)]-acetamide In the alternative, [(R)-1-(1,2,3,4-tetrahydro-isoquinolin-1-ylmethyl)]-acetamide can be prepared in analogy to step 4a using S-Xyliphos rather than R-Xyliphos.

[(R)-1-(1,2,3,4-tetrahydro-isoquinolin-1-ylmethyl)]-acetamide and [(S)-1-(1,2,3,4-tetrahydro-isoquinolin-1-ylmethyl)]-acetamide can be used in the further synthesis of compounds that are structurally very similar to Praziquantel or further be used in the synthesis of Praziquantel itself.

EXAMPLE 5

Examples Of Suitable Asymmetric Hydrogenation Conditions

Example 5.1

Preparation of 1-(1,2,3,4-tetrahydro-isoquinolin-1-ylmethyl)]-acetamide

The following Table 1 illustrates suitable exemplary asymmetric hydrogenation conditions for the preparation of [(R)-1-(1,2,3,4-tetrahydro-isoquinolin-1-ylmethyl)]-acetamide and/or [(S)-1-(1,2,3,4-tetrahydro-isoquinolin-1-ylmethyl)]-acetamide:

Under an inert atmosphere, iridium(I) cyclooctadiene chloride dimer (15.30 mg) and ligand (1 equivalent per iridium atom) were mixed in tetrahydrofuran (5.00 g). After 1 h stirring, this mixture was added to a solution of N-Isoquinolin-1-ylmethyl-acetamide (200.00 mg) in tetrahydrofuran (30.00 g). The blend was stirred under a 110 bar atmosphere of hydrogen overnight at 100° C. After evaporation of the solvent under reduced pressure, a mixture of (R)-(−)- and (S)-(+)-N-(1,2,3,4-Tetrahydro-isoquinolin-1-ylmethyl)-acetamide was obtained.

TABLE 1

| | Ir Catalyst Ligand | Pressure H$_2$ (bar) | Temp (° C.) | Conversion (%) | ee (%) |
|---|---|---|---|---|---|
| 1 | (R)-6,6'-Bis(diphenylphosphino)-2,2',3,3'-tetrahydro-5,5'-bi-1,4-benzodioxine | 105 | 100 | 61 | 36(R) |
| 2 | (S)-5,5'-Bis(di(3,5-xylyl)phosphino)-4,4'-bi-1,3-benzodioxole | 110 | 100 | 63 | 46(R) |
| 3 | (R)-7,7'-Bis[di(3,5-dimethylphenylphosphone]-2,2',3,3'-tetrahydro-1,1'-spirobiindane | 110 | 100 | 55 | 6(S) |
| 4 | (R)-1-{(S)-2-[Bis[3,5-di-trifluoromethylphenyl)phosphine]ferrocenyl}ethyldi-3,5-xylylphosphine | 110 | 75 | 53 | 18(S) |
| 5 | (S)-Xyliphos | 110 | 75 | 50 | 62(R) |
| 6 | (R)-Xyliphos | 110 | 100 | 78 | 84(S) |

Example 5.2

Preparation of 1-(1,2,3,4-tetrahydro-isoquinolin-1-ylmethyl)]-cyclohexanecarboxylic acid-amide The following Table 2 illustrates suitable asymmetric hydrogenation conditions, including catalysts, and also illustrates how the reaction conditions, for instance choice of solvent or additive, can be adjusted to optimize conversion and/or stereoselectivity, in particular in the preparation of [(R)-1-(1,2,3,4-tetrahydro-isoquinolin-1-ylmethyl)]-cyclohexanecarboxylic acid-amide and/or [(S)-1-(1,2,3,4-tetrahydro-isoquinolin-1-ylmethyl)]-cyclohexanecarboxylic acid-amide:

TABLE 2

1 Catalyst: (R)-Xyliphos 0.2 mmol,
catalyst loading 100/1 S/C, 30 bar H$_2$,
solvent 2 mL, [S] = 0.1M, 16 hours

| | Additive (mol %) | Solvent | Temp (° C.) | Conv (%) | Ee (%) |
|---|---|---|---|---|---|
| 1.1 | I$_2$ (5) | dioxane:DCM (20:1) | 80 | 46 | 73 (S) |
| 1.2 | I$_2$ (5) | dioxane:DCM (20:1) | 100 | 64 | 60 (S) |
| 1.3 | I$_2$ (5) | PhMe:DCM (20:1) | 80 | 64 | 69 (S) |
| 1.4 | I$_2$(50) | dioxane:DCM (20:1) | 100 | 99 | 77(S) |
| 1.5 | I$_2$ (100) | dioxane:DCM (20:1) | 100 | 100 | 80 (S) |
| 1.6 | I$_2$ (100) | dioxane:PhMe (20:1) | 100 | 100 | 76 (S) |
| 1.7 | I$_2$ (50) | dioxane:PhMe (20:1) | 100 | 100 | 54 (S) |
| 1.8 | I$_2$ (100) | dioxane:PhMe (20:1) | 80 | 100 | 84 (S) |

2 Catalyst: various (see below) 1 mmol,
catalyst loading 500/1 S/C, 30 bar H$_2$,
solvent 5 mL, [S] = 0.2M,
16 hours, I$_2$ 50 mol %, 100° C.

| | Catalyst | Solvent | Conv (%) | Ee (%) |
|---|---|---|---|---|
| 2.1 | (S)-Xyliphos | m-xylene | 79 | 79 (R) |
| 2.2 | (S)-Xyliphos | p-xylene | 100 | 80(R)) |
| 2.3 | (S)-Xyliphos | PhCF$_3$ | 97 | 82(R) |
| 2.4 | (R)-Xyl-BINAP | m-xylene | 100 | 70(R) |
| 2.5 | (R)-Xyl-BINAP | PhMe:DCM (4:1) | 97 | 76(R) |
| 2.6 | (R)-Xyl-BINAP | mesitylene | 93 | 67(R) |
| 2.7 | (R)-Xyl-BINAP | m-xylene-DCM (4:1) | 96 | 64(R) |
| 2.8 | (R)-Xyl-BINAP | m-xylene-DCM (3:2) | 98 | 50(R) |

3 Catalyst: various (see below) 0.05 mmol,
catalyst loading 50/1 S/C, 25 bar H$_2$,
solvent Dioxane:DCM 20:1 0.5 ml, [S] = 0.1M,
16 hours, 80° C., I$_2$ 50 mol %

| | Catalyst | Conv (%) | Ee (%) |
|---|---|---|---|
| 3.1 | (R)-(S$_p$)-Josiphos R1 = Ph R2 = Ph | 100 | 45 (R) |
| 3.2 | (R)-Xyliphos | 100 | 78 (S) |
| 3.3 | (R)-(S$_p$)-Taniaphos R1 = Ph R2 = Ph | 98 | 52(R) |
| 3.4 | (R)-Me-BoPhoz | 84 | 72(R) |
| 3.5 | (R)-Me-BoPhoz (3,5-F—Ph) | 27 | 68(R) |
| 3.6 | (R)-C3-TunePhos | 97 | 52(S) |
| 3.7 | (R)-Xyl-BINAP | 100 | 79(R) |

4 Catalyst: various (see below) 0.05 mmol,
catalyst loading 50/1 S/C, 25 bar H$_2$,
solvent mixture with: solvent:DCM 20:1 0.5 mL,
[S] = 0.1M, 16 hours, 80° C.

| | Catalyst | Additive 1 (mol %) | Additive 2 (mol %) | Solvent | Conv (%) | Ee (%) |
|---|---|---|---|---|---|---|
| 4.1 | (R)-Xyliphos | I$_2$ (50) | — | Me—THF | 100 | 81(S) |
| 4.2 | (R)-Xyliphos | I$_2$ (50) | — | THF | 99 | 77(S) |
| 4.3 | (R)-Xyliphos | I$_2$ (50) | — | IPA | 49 | 82(S) |
| 4.4 | (R)-Xyliphos | I$_2$ (50) | H$_3$PO$_4$ (100) | dioxane | 32 | 78(S) |
| 4.5 | (R)-Xyliphos | I$_2$ (50) | AcOH(100) | dioxane | 100 | 79(S) |
| 4.6 | (R)-Xyliphos | I$_2$ (50) | HI(100) | dioxane | 48 | 80(S) |
| 4.7 | (R)-Xyliphos | — | H$_3$PO$_4$ (100) | dioxane | 87 | 56(S) |
| 4.8 | (R)-Xyliphos | — | HI (100) | dioxane | 99 | 70(S) |
| 4.9 | (R)-Xyliphos | — | HBF$_4$ (100) | dioxane | 100 | 67(S) |
| 4.10 | (S)-Me-BoPhoz | I$_2$ (50) | — | dioxane | 89 | 75(S) |
| 4.11 | (S)-Me-BoPhoz | I$_2$ (50) | — | THF | 99 | 77(S) |
| 4.12 | (S)-Me-BoPhoz | I$_2$ (50) | — | Me—THF | 82 | 77(S) |
| 4.13 | (S)-Me-BoPhoz | I$_2$ (50) | — | EtOAc | 80 | 73(S) |
| 4.14 | (S)-Me-BoPhoz | — | H$_3$PO$_4$ (100) | dioxane | 45 | 72(S) |
| 4.15 | (S)-Me-BoPhoz | — | HI (100) | dioxane | 94 | 74(S) |
| 4.16 | (S)-Me-BoPhoz | — | HBF$_4$ (100) | dioxane | 63 | 67(S) |
| 4.17 | (R)-Xyl-BINAP | I$_2$ (50) | — | dioxane | 100 | 80(R) |
| 4.20 | (R)-Xyl-BINAP | I$_2$ (50) | — | THF | 100 | 78(R) |
| 4.21 | (R)-Xyl-BINAP | I$_2$ (50) | — | Me—THF | 95 | 78(R) |
| 4.22 | (R)-Xyl-BINAP | I$_2$ (50) | — | Ph—Me | 43 | 76(R) |
| 4.23 | (R)-Xyl-BINAP | I$_2$ (50) | — | EtOAc | 33 | 78(R) |
| 4.24 | (R)-Xyl-BINAP | I$_2$ (50) | H$_3$PO$_4$ (100) | dioxane | 97 | 79(R) |
| 4.25 | (R)-Xyl-BINAP | I$_2$ (50) | AcOH(100) | dioxane | 100 | 78(R) |

TABLE 2-continued

| | | | | | | |
|---|---|---|---|---|---|---|
| 4.26 | (R)-Xyl-BINAP | I$_2$ (50) | HI(100) | dioxane | 89 | 75(R) |
| 4.27 | (R)-Xyl-BINAP | — | HI (100) | dioxane | 95 | 81(R) |

| | Substr. Conc. [M] | Temp. [° C.] | Cat [mol %] | Conv (%) | Ee (%) |
|---|---|---|---|---|---|
| 5 Catalyst: (S)-Xyliphos 1 mmol, catalyst loading 200-500/1 S/C, 30 bar H$_2$, solvent dioxane 2-5 mL, [S] = 0.2-0.5M, 16 hours, I$_2$ 50 mol % | | | | | |
| 5.1 | 0.2 | 70 | 0.5 | 95 | 76(R) |
| 5.2 | 0.2 | 100 | 0.2 | 99 | 80(R) |
| 5.3 | 0.5 | 100 | 0.5 | 99 | 74(R) |
| 6 Catalyst: (R)-Xyl-BINAP 1 mmol, catalyst loading 200-500/1 S/C, 30 bar H$_2$, solvent dioxane 2-5 mL, [S] = 0.2-0.5M, 16 hours, I$_2$ 50 mol % | | | | | |
| 6.1 | 0.2 | 100 | 0.2 | 99 | 78(R) |
| 6.2 | 0.5 | 100 | 0.5 | 100 | 71(R) |

The invention claimed is:

1. A method of preparing (i) an optically active compound according to the following Formula (X1)

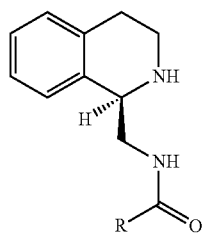

(X1)

or (ii) an optically active compound according to the following Formula (X2)

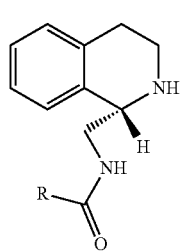

(X2)

or (iii) a mixture of the two, wherein R is C$_1$-C$_8$ alkyl, C$_3$-C$_8$ cycloalkyl, or unsubstituted or substituted aryl, comprising:

subjecting a compound according to the following Formula (Y)

(Y)

with R as above, to a hydrogenation step.

2. The method according to claim 1, wherein R is methyl or cyclohexyl.

3. The method according to claim 1, wherein the mixture comprises either the compound according to Formula (X1) or the compound according to Formula (X2) in excess and wherein the hydrogenation step is an asymmetric hydrogenation step in the presence of a catalyst.

4. The method according to claim 3, wherein the compound according to Formula (X1) is present in the mixture in an enantiomeric excess of at least 10%.

5. The method according to claim 3, wherein the catalyst is an iridium based catalyst.

6. The method according to claim 5, wherein the catalyst comprises an iridium compound in combination with a chiral phosphine ligand.

7. The method according to claim 5, wherein the iridium based catalyst is or comprises a mixture of [Ir(COD)Cl]$_2$ and one of the following ligands:

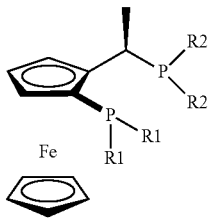

(R)-(S$_p$)-Josiphos

-continued

R1 = t-Bu         R2 = Ph
R1 = Ph           R2 = Ph
R1 = Ph           R2 = Xylyl (=(R)-Xyliphos)
         (S)-(R$_p$)-Josiphos
R1 = t-Bu         R2 = Ph
R1 = Ph           R2 = Ph
R1 = Ph           R2 = Xylyl (=(S)-Xyliphos)

(R)-BoPhoz
(R)-Me-BoPhoz:           R = Me, R' = Ph
(R)-Me-BoPhoz (Xyl):     R = Me, R' = Xylyl
(R)-Me-BoPhoz (3,5-F—Ph) R = Me, R' = 3,5-F—Ph
         (S)-BoPhoz
(S)-Me-BoPhoz:           R = Me, R' = Ph
(S)-Me-BoPhoz (Xyl):     R = Me, R' = Xylyl
(S)-Me-BoPhoz (3,5-F—Ph) R = Me, R' = 3,5-F—Ph (R)-(S$_p$)-Taniaphos
(R)-1-[(S$_p$)-α-(Dimethylamino-2-
(diphenylphosphino)benzyl]-
2-diphenylphosphinoferrocene
         R1 = Ph R2 = Ph
(S)-(R$_p$)-Taniaphos
(S)-1-[(R$_p$)-α-(Dimethylamino-2-
(diphenylphosphino)benzyl]-
2-diphenylphosphinoferrocene
         R1 = Ph R2 = Ph (R)-Xylyl-BINAP
   Ar = 3,5-Me$_2$—Ph
(S)-Xylyl-BINAP
   Ar = 3,5-Me$_2$—Ph (R)-6,6'-Bis(diphenylphosphino)-2,2',3,3'-tetrahydro-
5,5'-bi-1,4-benzodioxine
(S)-6,6'-Bis(diphenylphosphino)-2,2',3,3'-tetrahydro-
5,5'-bi-1,4-benzodioxine (S)-5,5'-Bis(di(3,5-xylyl)phosphino)-4,4'-bi-1,3-benzodioxole
(R)-5,5'-Bis(di(3,5-xylyl)phosphino)-4,4'-bi-1,3-benzodioxole (R)-7,7'-Bis[di(3,5-dimethylphenylphosphino]-2,2',3,3'-
tetrahydro-1,1'-spirobiindane
(S)-7,7'-Bis[di(3,5-dimethylphenylphosphino]-2,2',3,3'-
tetrahydro-1,1'-spirobiindane (R)-1-{(S)-2-[Bis[3,5-di-trifluoromethylphenyl)phosphino]ferrocenyl}ethyldi-3,5-xylylphosphine
(S)-1-{(R)-2-[Bis[3,5-di-trifluoromethylphenyl)phosphino]ferrocenyl}ethyldi-3,5-xylylphosphine
(R)-C3-TunePhos
(R)-1,13-Bis(diphenylphosphino)-7,8-dihydro-6H-dibenzo[f,h][1,5]dioxonin
(S)-C3-TunePhos
(S)-1,13-Bis(diphenylphosphino)-7,8-dihydro-6H-dibenzo[f,h][1,5]dioxonin.

8. The method according to claim 3, wherein the asymmetric hydrogenation step in the presence of a catalyst is carried out involving at least one of:
elevated temperature;
a solvent, which is dioxane, THF, Me-THF, IPA, DCE, DCM, ethyl acetate, toluene, α,α,α-trifluorotoluene, xylene, mesitylene or a mixture of any two or more thereof;
at least one additive;
a substrate concentration of at least 0.05 mmol/l;
a catalyst loading of at least 50/1 substrate/catalyst; and
elevated pressure.

9. A method of preparing an enantiomerically pure or enantiomerically enriched compound according to Formula (Q1) or Formula (Q2)

comprising
(a) preparing according to the method of claim 1 (i) the optically active compound according to Formula (X1) or (iii) the mixture of compounds according to Formula (X1) and Formula (X2), in which mixture the compound according to Formula (X1) is present in excess, for the preparation of the compound according to Formula (Q1)
or
(b) preparing according to the method of claim 1 (i) the optically active compound according to the Formula (X2) or (iii) the mixture of compounds according to Formula (X1) and Formula (X2), in which mixture the compound according to Formula (X2) is present in excess, for the preparation of the compound according to Formula (Q2),
wherein R in Formulae (Q1) and (Q2) is selected from the group consisting of $C_1$-$C_8$ alkyl, $C_3$-$C_8$ cycloalkyl, and optionally substituted aryl.

10. The method of preparing the enantiomerically pure or enantiomerically enriched compound according to Formula (Q1) or Formula (Q2) according to claim 9, further comprising
(a) reacting (i) the optically active compound according to Formula (X1) or (iii) the mixture of compounds according to Formula (X1) and Formula (X2), in which mixture the compound according to Formula (X1) is present in excess, with a compound Y—CO—$CH_2$—X, wherein Y is F, Cl or Br or —O—CO-alkyl and X is F, Cl or Br, to give the compound according to Formula (Q1);
or
(b) reacting the optically active compound according to the Formula (X2) or (iii) the mixture of compounds according to Formula (X1) and Formula (X2), in which mixture the compound according to Formula (X2) is present in excess, with a compound Y—CO—$CH_2$—X, wherein Y is F, Cl or Br or —O—CO-alkyl and X is F, Cl or Br, to give the compound according to Formula (Q2).

11. A method of preparing an enantiomerically pure or enantiomerically enriched compound according to Formula (Q1) or Formula (Q2)

comprising preparing a mixture of compounds according to Formula (X1) and Formula (X2) according to the method of claim 1,
separating the compound according to Formula (X1) from the compound according to Formula (X2), and reacting
(a) the compound according to Formula (X1) with a compound Y—CO—CH$_2$—X, wherein Y is F, Cl or Br or —O—CO-alkyl and X is F, Cl or Br, to obtain the enantiomerically pure or at least enantiomerically enriched compound according to Formula (Q1); or
(b) the compound according to Formula (X2) with a compound Y—CO—CH$_2$—X, wherein Y is F, Cl or Br or —O—CO-alkyl and X is F, Cl or Br, to obtain the enantiomerically pure or at least enantiomerically enriched compound according to Formula (Q2), wherein R is the same in Formulae (Q1) and (Q2) as in Formulae (X1) and (X2).

12. A method of preparing enantiomerically pure or enantiomerically enriched (R)-Praziquantel

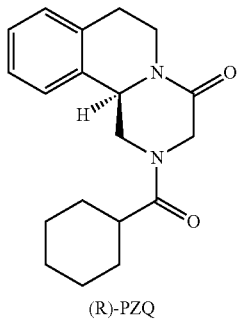 [SMILES: O=C(C1CCCCC1)N1CC(=O)N2CCc3ccccc3[C@@H]2C1]

(R)-PZQ comprising preparing by the method according to claim 9, the optically active compound according to Formula (X1) or (iii) the mixture of compounds according to Formula (X1) and Formula (X2), in which mixture the compound according to Formula (X1) is present in excess, wherein R is cyclohexyl in the compound according to Formula (X1).

13. A method of preparing a mixture of an optically active compound according to the following Formula (X1) and an optically active compound according to the following Formula (X2)

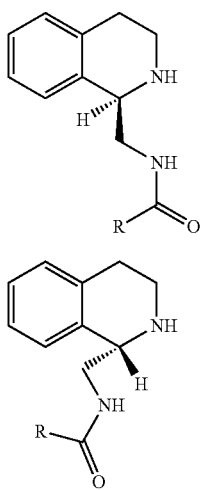

or a salt thereof, wherein R is selected from the group consisting of C$_1$-C$_8$ alkyl and C$_3$-C$_8$ cycloalkyl;
wherein the compounds or salt(s) thereof are present in said mixture in a first ratio of RM1=X1:X2, which is from 0.8 to 1.2;
comprising the following steps:
(a) dehydrogenating a mixture of compounds according to Formulae (X1) and (X2), wherein the compounds are present in said mixture in a second ratio RM2=X1:X2, which is either smaller than 0.8 or larger than 1.2, to produce a mixture of compounds according to the following Formula (Y) and to Formula (Z), wherein R is the same as in Formulae (X1) and (X2)

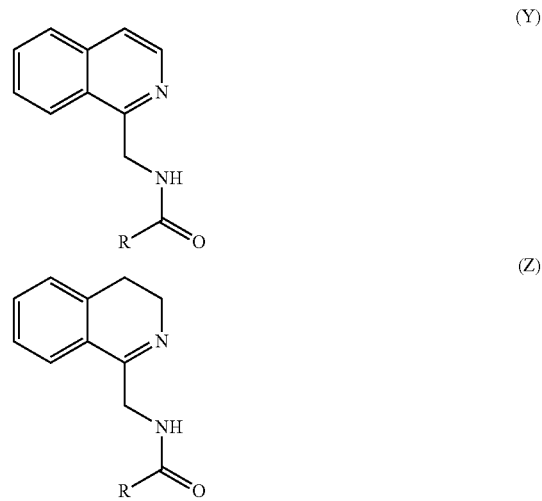

or salt(s) thereof and
(b) hydrogenating said mixture of compounds according to Formula (Y) and to Formula (Z) or salt(s) thereof to obtain the mixture of compounds of Formulae (X1) and (X2) or salt(s) thereof in the first ratio RM1,
wherein the mixture of compounds according to Formulae (X1) and (X2) or salt(s) thereof in the second ratio RM2 is optionally prepared either by asymmetric hyrogenation of a compound according to Formula (Y) in accordance with the method according to claim 3 or by separation of a mixture of compounds according to Formulae (X1) and (X2).

14. A compound according to the following Formula (Y1)

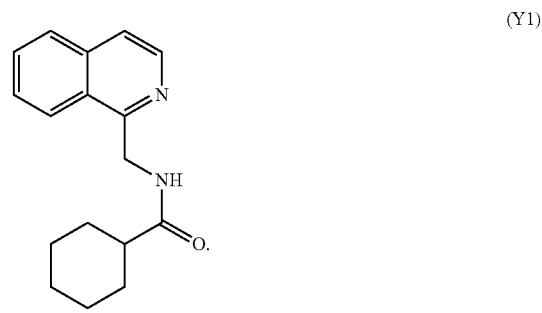 [SMILES: O=C(NCc1nccc2ccccc12)C1CCCCC1]

15. A method
for the preparation of
(i) an optically active compound according to the following Formula (X1)

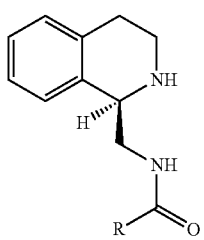

or (ii) an optically active compound according to the following Formula (X2)

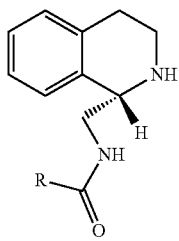

or (iii) a mixture of the two, wherein R is selected from the group consisting of $C_1$-$C_8$ alkyl, $C_3$-$C_8$ cycloalkyl, and optionally substituted aryl, comprising a reaction of a compound of Formula (Y)

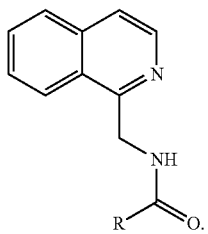

16. A method for the preparation of (R)-Praziquantel comprising a reaction of a compound of Formula (Y1) according to claim 14.

17. A method of preparing a compound of Formula (Y1) according to claim 14

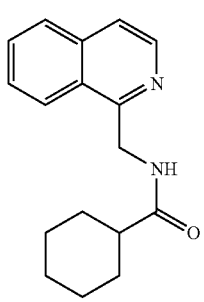

comprising reacting [isoquinolin-1-yl)-methyl]-amine

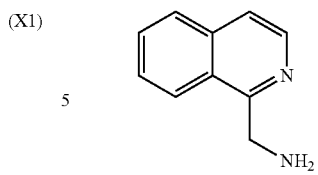

with a cyclohexane carboxylic acid based acylating agent.

18. The method according to claim 3, wherein the compound according to Formula (X1) is present in the mixture in an enantiomeric excess of at least 80%.

19. The method according to claim 3, wherein the asymmetric hydrogenation step in the presence of a catalyst is carried out involving at least one of:

elevated temperature of at least 60° C.;

at least one additive, which is iodine ($I_2$), iodide, phosphoric acid ($H_3PO_4$), acetic acid (AcOH), HI, or $HBF_4$, in an amount of at least 5 mol %;

a substrate concentration of at least 10 mmol/l;

a catalyst loading of at least 100/1 substrate/catalyst; and elevated pressure of at least 1 bar $H_2$.

20. A method of preparing a mixture of an optically active compound according to the following Formula (X1) and an optically active compound according to the following Formula (X2)

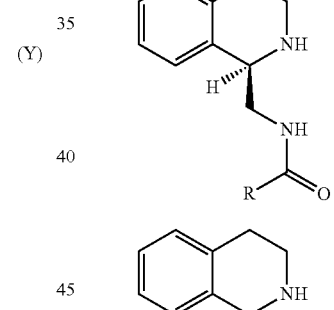

or a salt thereof, wherein R is selected from the group consisting of $C_1$-$C_8$ alkyl and $C_3$-$C_8$ cycloalkyl;

wherein the compounds or salt(s) thereof are present in said mixture in a first ratio of RM1=X1:X2, which is from 0.8 to 1.2; comprising the following steps:

(c) dehydrogenating a mixture of compounds according to Formulae (X1) and (X2), wherein the compounds are present in said mixture in a second ratio RM2=X1:X2, which is either smaller than 0.8 or larger than 1.2, to produce a mixture of compounds according to the following Formula (Y) and to Formula (Z), wherein R is the same as in Formulae (X1) and (X2)

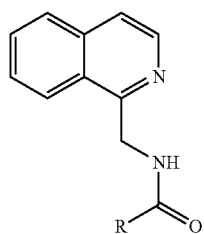

(Y)

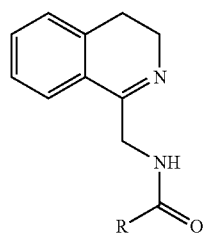

(Z)

or salt(s) thereof and (d) hydrogenating said mixture of compounds according to Formula (Y) and to Formula (Z) or salt(s) thereof to obtain the mixture of compounds of Formulae (X1) and (X2) or salt(s) thereof in the first ratio RM1, wherein the mixture of compounds according to Formulae (X1) and (X2) or salt(s) thereof in the second ratio RM2 is prepared by asymmetric hyrogenation of a compound according to Formula (Y) in accordance with the method according to claim 3.

* * * * *